United States Patent
Nagaya et al.

(10) Patent No.: US 10,167,453 B2
(45) Date of Patent: Jan. 1, 2019

(54) SACCHARIDE OXIDASE, AND PRODUCTION METHOD FOR SAME AND USE OF SAME

(71) Applicant: AMANO ENZYME INC., Nagoya-shi Aichi (JP)

(72) Inventors: Miho Nagaya, Kakamigahara (JP); Akiko Sugita, Kakamigahara (JP); Naoki Matsumoto, Kakamigahara (JP); Masamichi Okada, Kakamigahara (JP)

(73) Assignee: AMANO ENZYME INC., Nagoya-Shi (JP)

(*) Notice: Subject to any disclaimer, the term of this patent is extended or adjusted under 35 U.S.C. 154(b) by 0 days.

(21) Appl. No.: 15/412,757

(22) Filed: Jan. 23, 2017

(65) Prior Publication Data

US 2017/0137788 A1    May 18, 2017

Related U.S. Application Data

(62) Division of application No. 14/428,105, filed as application No. PCT/JP2013/074810 on Sep. 13, 2013, now abandoned.

(30) Foreign Application Priority Data

Sep. 14, 2012  (JP) .................. 2012-203530

(51) Int. Cl.
| | |
|---|---|
| C12N 9/04 | (2006.01) |
| C12N 15/53 | (2006.01) |
| C12N 1/15 | (2006.01) |
| C12P 7/58 | (2006.01) |
| A21D 8/04 | (2006.01) |
| A23J 1/00 | (2006.01) |
| A23J 3/04 | (2006.01) |
| C12P 19/12 | (2006.01) |
| A23L 29/00 | (2016.01) |
| A23L 15/00 | (2016.01) |
| C12N 15/52 | (2006.01) |
| A23L 5/00 | (2016.01) |

(52) U.S. Cl.
CPC .......... *C12N 9/0006* (2013.01); *A21D 8/042* (2013.01); *A23J 1/008* (2013.01); *A23J 3/04* (2013.01); *A23L 15/25* (2016.08); *A23L 29/06* (2016.08); *C12N 15/52* (2013.01); *C12P 7/58* (2013.01); *C12P 19/12* (2013.01); *C12Y 101/03004* (2013.01); *A23L 5/00* (2016.08); *A23V 2002/00* (2013.01)

(58) Field of Classification Search
None
See application file for complete search history.

(56) References Cited

U.S. PATENT DOCUMENTS 2,783,150 A    2/1957   Luther et al. ................. 99/93

FOREIGN PATENT DOCUMENTS

| CA | 2012723 | 3/1990 |
|---|---|---|
| CN | 1976593 A | 6/2007 |
| JP | 4-84848 A | 3/1992 |
| JP | 5-84074 A | 4/1993 |
| JP | 7-67649 A | 3/1995 |
| JP | 2001-526058 A | 12/2001 |
| JP | 3310008 B2 | 7/2002 |
| WO | WO 96/39851 A1 | 12/1996 |
| WO | WO 99/31990 A1 | 7/1999 |
| WO | WO 2005/104859 A2 | 11/2005 |
| WO | WO 2011/009747 A1 | 1/2011 |
| WO | WO 2012/116431 A1 | 9/2012 |

OTHER PUBLICATIONS

Sang, H., Mechanisms of Development 121:1179-1186, 2004.*
Dictionary definition of "recombinant vector", obtained from www.thefreedictionary.com, 1 page, last viewed on Feb. 16, 2018.*
Biochimica Biophysica Acta, 1991, vol. 1118, p. 41-47.
Biochem. Biophys. Res. Commun., 1992, vol. 186, No. 1, p. 40-46.
Agric. Biol. Chem., 1991, vol. 55, No. 2, p. 471-477.
Biotechnology and Bioengineering, 2000. 04, vol. 68, No. 2, p. 231-237.
International Search Report dated Oct. 22, 2013, issued to the corresponding International Application No. PCT/JP2013/074810.
European Office Action with extended search report dated Feb. 5, 2016, issued by the European Patent Office in corresponding application 13837354.3.
Maryam Foumani et al., "Altered Substrate Specificity of the Gluco-Oligosaccharide Oxidase From *Acremonium strictum*", vol. 108, No. 10, Oct. 2011, pp. 2261-2269.
Lobzov K.I. et al., "Preservation of dried egg white using propionic acid bacteria". (Abstract Only) 1979.
First Examination Report dated Aug. 3, 2017, issued to New Zealand Application No. 706007 issued by the New Zealand Office.
C. Sisak et al., Elimination of glucose in egg white using immobilized glucose oxidase, Feb. 7, 2006, Enzyme and Microbial Technology.
European Office Action dated Oct. 27, 2017, issued by the European Patent Office in corresponding application EP 13 837 354.3.

* cited by examiner

*Primary Examiner* — David Steadman
(74) *Attorney, Agent, or Firm* — Stein IP, LLC

(57) ABSTRACT

A protein having a novel saccharide oxidase activity capable of being subjected to various uses is provided. The present invention provides a protein having the following physicochemical characteristics: (1) effect: oxidizing a saccharide to produce a saccharic acid; (2) substrate specificity: acting on glucose, maltotriose, maltose, galactose, maltotetraose, lactose, and cellobiose; and, (3) [Km value of glucose]/[Km value of maltose]≤1.

8 Claims, 8 Drawing Sheets

Specification includes a Sequence Listing.

10,167,453 B2

SACCHARIDE OXIDASE, AND PRODUCTION METHOD FOR SAME AND USE OF SAME

CROSS-REFERENCE TO RELATED APPLICATIONS

This application is a divisional of U.S. application Ser. No. 14/428,105, filed Mar. 13, 2015, which is a national stage of International Application No. PCT/JP2013/074810, filed Sep. 13, 2013, which claims the benefit of priority to Japanese Application No. 2012-203530, filed Sep. 14, 2012, in the Japanese Patent Office, the disclosures of which are incorporated herein in their entireties by reference.

TECHNICAL FIELD

The present invention relates to a protein having a saccharide oxidase activity. More particularly, it relates to a protein having a saccharide oxidase activity which acts on a wide range of saccharides, a gene encoding the protein, a recombinant vector containing the gene, a transformant, and a method for producing the aforementioned protein, as well as use of the aforementioned protein.

BACKGROUND ART

A representative enzyme oxidizing saccharide is a glucose oxidase which oxidizes glucose, and such a glucose oxidase is widely used in various fields.

For example in a dry egg white manufacturing process, a glucose oxidase is used for the purpose of removing the glucose in the egg white (desugaring). Since the dry egg white can be stored for a longer period when compared with a raw egg white and enables a lower cost for transportation and a smaller space for storage, it is used as a starting material for various food products. The glucose contained in such a dry egg white undergoes a reaction with an amino group in the egg protein during the storage to allow a Maillard reaction to occur, resulting in a brown color and an unpleasant odor. In order to avoid such a deterioration of the quality, a fermentation method using glucose oxidases or yeast for the purpose of removing of the glucose in the egg white is used.

On the other hand, the glucose oxidase has a relatively high thermostability, which allows the glucose oxidase activity to remain in a product. For example, when the glucose oxidase activity remains in the dry egg white, it results in a problematic oxidization of the glucose in a starting material during the manufacture of confectioneries using the dry egg white. On the contrary, a heat treatment under a condition allowing the glucose oxidase to be inactivated results in coagulation of the egg white, which leads to a problematic deterioration of the commercial value of the dry egg white. The desugaring by fermentation of the yeast also results in a problem due to a fermentation odor remaining in the dry egg white product.

Also in a bakery or flour milling plant, for enhancing the sintering performance of a flour or for making a kneaded flour having desirable strength and stability by improving the elasticity, a glucose oxidase is used. This effect is believed to be supported by a mechanism in which the glucose in the flour mixture is oxidized to produce gluconolacton and hydrogen peroxide and the hydrogen peroxide thus produced acts as an oxidizer thereby contributing to the formation of a gluten S—S bond. As a result, the protein acquires a further stable form, thereby improving the quality of the kneaded flour, the capacity of the sintered product, and the core structure.

For example, Patent Document 1 typically discloses a technology which involves addition of a glucose oxidase to a cereal flour to improve the rheological characteristics of the kneaded flour, texture and appearance of the sintered bread. Also in Patent Document 2, a preparation for improving the quality of a bread containing a cellulase and a glucose oxidase is disclosed. In addition, Patent Document 3 discloses a bread improver containing a glucose oxidase and a lipase and a baking method using the same.

While the glucose oxidase is used in various applications as described above, it is problematically less effective on a material containing no or small amount of glucose because it is an enzyme which oxidizes the glucose exclusively. In addition, no effect can be achieved when another saccharide such as lactose is contained unless an enzyme capable of decomposing such another saccharide into the glucose, such as a lactase, is used in combination.

For example, use of a glucose oxidase as an additive for improving a kneaded flour and a bread requires the presence of glucose as a substrate, whose content in a wheat flour is as low as 0 to 0.4% by weight, which poses a limitation of the usefulness of the glucose oxidase. On the other hand, a maltose content of the flour of a cereal plant is known to be higher than the glucose content.

For the purpose of solving the aforementioned problems, much attention has been focused on a saccharide oxidase effective on saccharides other than the glucose. For example, Patent Document 4 discloses a technology relating to an oligosaccharide oxidase exhibiting a satisfactory reaction activity on respective substrates of D-glucose, D-lactose, D-cellobiose, D-maltotriose, D-maltotetraose, D-maltopentaose, D-maltohexaose, and D-maltoheptaose. In addition, Patent Document 5 discloses a technology for improving the characteristics of a dough or a bread by using a saccharide oxidase derived from a microorganism belonging to genus Microdochium which oxidizes a maltodextrin or a cellodextrin preferentially over the glucose.

CITATION LIST

Patent Literature

[Patent Document 1] U.S. Pat. No. 2,783,150
[Patent Document 2] Canada Patent No. 2012723
[Patent Document 3] JP-A No. H04-84848
[Patent Document 4] JP-A No. H05-84074
[Patent Document 5] JP-T No. 2001-526058

SUMMARY OF INVENTION

Technical Problem

Any enzyme, which can oxidize disaccharides or higher saccharides in addition to monosaccharides such as glucose, is expected to be used in a wider field when compared with a glucose oxidase.

Accordingly, a major object of the present invention is to provide a novel protein having a saccharide oxidase activity capable of being applied to various uses.

Solution to Problem

As a result of our intensive study to search for a protein having a saccharide oxidase activity, we were successful in producing a protein having an appropriate thermostability, thereby accomplishing the present invention.

Accordingly, the present invention provides the following [1] to [32].

[1] A protein having the following physicochemical characteristics:
(1) effect: oxidizing a saccharide to a saccharic acid;
(2) substrate specificity: acting on glucose, maltotriose, maltose, galactose, maltotetraose, lactose, and cellobiose; and,
(3) [Km value of glucose]/[Km value of maltose]≤1.

[2] The protein according to [1] wherein 0.4 [Km value of glucose]/[Km value of maltose]≤1.

[3] A protein having the following physicochemical characteristics:
(1) effect: oxidizing a saccharide to a saccharic acid;
(2) substrate specificity: acting on glucose, maltotriose, maltose, galactose, maltotetraose, lactose, and cellobiose; and,
(3) molecular weight: about 63 kDa (measurement by SDS-PAGE method).

[4] The protein according to [3] wherein [Km value of glucose]/[Km value of maltose]≤1.

[5] The protein according to [4] wherein 0.4≤[Km value of glucose]/[Km value of maltose]≤1.

[6] A protein having the following physicochemical characteristics:
(1) effect: oxidizing a saccharide to a saccharic acid;
(2) substrate specificity: acting on glucose, maltotriose, maltose, galactose, maltotetraose, lactose, and cellobiose;
(3) optimum pH: 5.0 to 9.0;
(4) stable pH range: 5.0 to 10.5;
(5) optimum temperature: 20° C. to 55° C.;
(6) thermostability: stable at 45° C. or lower; and,
(7) molecular weight: about 63 kDa (measurement by SDS-PAGE method).

[7] The protein according to [6] wherein [Km value of glucose]/[Km value of maltose]≤1.

[8] The protein according to [7] wherein 0.4 [Km value of glucose]/[Km value of maltose]≤1.

[9] An *Acremonium* microorganism-derived protein having the following physicochemical characteristics:
(1) effect: oxidizing a saccharide to a saccharic acid;
(2) substrate specificity: acting on glucose, maltotriose, maltose, galactose, maltotetraose, lactose, and cellobiose; and,
(3) [Km value of glucose]/[Km value of maltose]≤1.

[10] The protein according to [9] wherein 0.4 [Km value of glucose]/[Km value of maltose]≤1.

[11] An *Acremonium* microorganism-derived protein having the following physicochemical characteristics:
(1) effect: oxidizing a saccharide to a saccharic acid;
(2) substrate specificity: acting on glucose, maltotriose, maltose, galactose, maltotetraose, lactose, and cellobiose; and,
(3) molecular weight: about 63 kDa (measurement by SDS-PAGE method).

[12] The protein according to [11] wherein [Km value of glucose]/[Km value of maltose]≤1.

[13] The protein according to [12] wherein 0.4 [Km value of glucose]/[Km value of maltose]≤1.

[14] An *Acremonium* microorganism-derived protein having the following physicochemical characteristics:
(1) effect: oxidizing a saccharide to a saccharic acid;
(2) substrate specificity: acting on glucose, maltotriose, maltose, galactose, maltotetraose, lactose, and cellobiose; and,
(3) optimum pH: 5.0 to 9.0;
(4) pH stability: 5.0 to 10.5;
(5) optimum temperature: 20° C. to 55° C.;
(6) thermostability: stable at 45° C. or lower; and,
(7) molecular weight: about 63 kDa (measurement by SDS-PAGE method).

[15] The protein according to [14] wherein [Km value of glucose]/[Km value of maltose]≤1.

[16] The protein according to [15] wherein 0.4 [Km value of glucose]/[Km value of maltose]≤1.

[17] The protein according to [9] to [16] wherein the aforementioned *Acremonium* microorganism is *Acremonium chrysogenum*.

[18] A protein described in the following (a), (b), or (c):
(a) a protein consisting of the amino acid sequence represented by SEQ. ID. NO:10;
(b) a protein consisting of an amino acid sequence resulting from deletion, substitution, and/or addition of one to several amino acids in the amino acid sequence represented by SEQ. ID. NO:10 and having a saccharide oxidase activity; and,
(c) a protein consisting of an amino acid sequence having a homology of 90% or more with the amino acid sequence represented by SEQ. ID. NO:10 and having a saccharide oxidase activity.

[19] A gene encoding the protein according to [18].

[20] A gene consisting of the DNA described in the following (a), (b), or (c):
(a) a DNA consisting of the base sequence represented by SEQ. ID. NO:6;
(b) a DNA consisting of a base sequence resulting from deletion, substitution, and/or addition of one to several bases in the base sequence represented by SEQ. ID. NO:6 and encoding a protein having a saccharide oxidase activity; and,
(c) a DNA consisting of a base sequence having a homology of 90% or more with the base sequence represented by SEQ. ID. NO:6 and encoding a protein having a saccharide oxidase activity.

[21] A gene consisting of the DNA described in the following (a), (b), or (c):
(a) a DNA consisting of the base sequence represented by SEQ. ID. NO:9;
(b) a DNA consisting of a base sequence resulting from deletion, substitution, and/or addition of one to several bases in the base sequence represented by SEQ. ID. NO:9 and encoding a protein having a saccharide oxidase activity; and,
(c) a DNA consisting of a base sequence having a homology of 90% or more with the base sequence represented by SEQ. ID. NO:9 and encoding a protein having a saccharide oxidase activity.

[22] A recombinant vector containing the gene according to any one of [19] to [21].

[23] A transformant resulting from transformation of a host cell with the recombinant vector according to [22].

[24] A method for producing a protein by collecting the protein according to any one of [1] to [18] from a culture obtained by culturing a microorganism having an ability of producing the protein according to any one of [1] to [18] in a nutrient medium.

[25] A method for producing a protein by culturing the transformant according to [23] in a culture medium and collecting a protein having a saccharide oxidase activity from the culture.

[26] A method for producing a saccharic acid comprising producing the saccharic acid from a saccharide using the protein according to any one of [1] to [18].

[27] Use of the protein according to any one of [1] to [18] for oxidizing a saccharide in a food product.

[28] A method for desugaring egg white comprising at least using the protein according to [27].

[29] A method for producing a desugared egg white using the desugaring method according to [28].

[30] A method for improving the quality of a bread and/or the physical property of a dough comprising at least using the protein according to [27].

[31] A method for producing a bread comprising using the improvement method according to [30].

[32] A method for producing lactobionic acid comprising at least using the protein according to [27].

Advantageous Effects of Invention

Since the protein according to the present invention acts on a wide range of saccharides and also has an appropriate thermostability, it can allow the saccharide oxidase effect to function in a wide range of the fields where existing glucose oxidases or oligosaccharide oxidases could not be useful.

DESCRIPTION OF EMBODIMENTS

Figure 1:
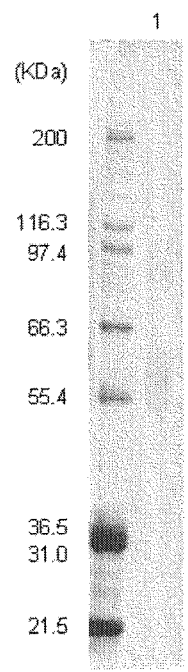
FIG. 1 is a drawing-substituting graph exhibiting an SDS-PAGE of the saccharide oxidase in Example 1. Lane 1: Saccharide oxidase.

The followings are the detailed descriptions of the embodiments which are preferable for practicing the present invention. The embodiments described below are only examples of the representative embodiments of the present invention, by which the scope of the present invention is not interpreted narrowly.

<1. A Protein Having a Saccharide Oxidase Activity>

The protein according to the present invention is a protein having the physicochemical characteristics described below.

In the present invention, the method for measuring the saccharide oxidase activity is not limited particularly, and any known method can be selected and performed. In the present invention, the saccharide oxidase activity was measured by the methods indicated in Examples described below.

(1) Effects

The protein according to the invention oxidizes a saccharide described below in the presence of oxygen to produce a saccharic acid. Particularly, when the protein according to the present invention is allowed to act on the saccharide described below in the presence of oxygen, a saccharic acid and hydrogen peroxide are produced.

(2) Substrate Specificity

The protein according to the present invention exhibits the activity on glucose, maltotriose, maltose, galactose, maltotetraose, lactose, and cellobiose. The relative activity of the protein according to the present invention toward each substrate, when the activity toward the glucose being regarded as 100%, is about 92% toward the maltotriose, about 86% toward the maltose, about 79% toward the galactose, about 60% toward the maltotetraose, about 58% toward the lactose, and about 53% toward the cellobiose (see Example 2 described below).

It is noted, in the present invention, that if the relative activity is 50% or higher when the activity toward the glucose as a substrate is used as a standard (100%) then it is judged that "the substrate is one on which the present enzyme act satisfactorily".

Thus, the protein according to the present invention exhibits its activity toward a wide range of saccharides including disaccharides or higher ones in addition to the monosaccharides such as the glucose. As a result, it is possible to allow the saccharide oxidase effect to function in a wide range of the fields where existing glucose oxidases or oligosaccharide oxidases could not be useful.

(3) Km Values

In the present invention, the typical method for calculating the Km value of a protein (Michaelis constant) is not limited particularly, and any known method can be selected for the calculation. In the present invention, Km values were calculated especially by the method indicated in Example 8 described below. While the Km value of the protein according to the present invention is not limited particularly, it is preferable that [Km value of glucose]/[Km value of maltose] ≤1, and it is more preferable that 0.4 [Km value of glucose]/[Km value of maltose]≤1.

(4) Molecular Weight

The protein according to the present invention has a molecular weight, when measured by an SDS-PAGE method, of about 63 kDa.

(5) Optimum pH

The protein according to the present invention exhibits the highest saccharide oxidase activity at a pH around 5.0 to 9.0 under the reaction conditions involving 37° C. for 5 minutes.

(6) pH Stability

The protein according to the present invention is stable at a pH around 5.0 to 10.5 under the treatment conditions involving 37° C. for 15 minutes.

(7) Optimum Temperature

The protein according to the present invention exhibits the highest saccharide oxidase activity around 20° C. to 55° C. under the reaction conditions involving pH7.0 for 5 minutes.

(8) Thermostability

The protein according to the present invention maintains an activity of 80% or higher even when treated at a temperature up to 45° C. under the treatment conditions involving pH7.0 for 15 minutes.

(9) Source

Since the protein according to the present invention described above has a heretofore unidentified property in the aforementioned physicochemical characteristics, any protein specified by the aforementioned physicochemical characteristics can be used regardless of the source from which it is derived. In the present invention, those derived from microorganisms belonging to genus *Acremonium* may be exemplified. In such a case, the microorganism belonging to genus *Acremonium* may for example be *Acremonium chrysogenum*.

As used herein, "a saccharide oxidase derived from *Acremonium chrysogenum*" is a saccharide oxidase produced by a microorganism classified into *Acremonium chrysogenum* (which may be wild type or mutant), or a saccharide oxidase obtained by a gene engineering method utilizing a saccharide oxidase gene. Accordingly, a recombinant produced by a host microorganism transduced with a saccharide oxidase gene obtained from *Acremonium chrysogenum* (or a gene modified therefrom) is regarded also to be "a saccharide oxidase derived from *Acremonium chrysogenum*".

Examples of *Acremonium chrysogenum* from which the protein according to the present invention is derived include *Acremonium chrysogenum* NBR C30055 (NITE, Japan), ATCC15006 (ATCC, United States), and DSM880 (DSMZ, Germany).

(10) Amino Acid Sequence

Since the protein according to the present invention has a heretofore unidentified property in the aforementioned physicochemical characteristics, its amino acid structure is not limited as far as it is a protein specified by the aforementioned physicochemical characteristics, and it can be specified for example by the following amino acid sequences.

Typically, the protein according to the present invention can be specified by the amino acid sequence represented by SEQ. ID. NO:10.

Herein, in general, when a part of the amino acid sequence of a certain protein is modified, the modified protein may sometimes have a function the same as that of the protein before modification. That is to say, the modification of the amino acid sequence does not have a substantial effect on the function of the protein, so that the function of the protein may be maintained before and after the modification. Accordingly, the present invention provides, as another embodiment, a protein consisting of an amino acid sequence resulting from deletion, substitution, and/or addition of one to several amino acids in the amino acid sequence represented by SEQ. ID. NO:10 and having a saccharide oxidase activity. "The deletion, substitution, and/or addition of one to several amino acids constituting the amino acid sequence" refers typically to a partial difference in the amino acid sequence.

Herein, the difference in the amino acid sequence is permitted as long as the saccharide oxidase activity is maintained (more or less change in the activity is permitted). As long as this condition is satisfied, the position in which a difference in the amino acid sequence occurs is not particularly limited and the difference may occur in a plurality of positions. The plurality herein signifies a numerical value corresponding to less than about 30%, preferably less than about 20%, further preferably less than about 10%, still further preferably less than about 5%, and most preferably less than about 1% with respect to the total amino acid.

Thus, it means that there is an identity for example of about 70% or more, preferably about 80% or more, more preferably about 90% or more, further preferably about 95% or more, and most preferably about 99% or more with the amino acid sequence represented by SEQ. ID. NO:10.

Preferably, an equivalent protein is obtained by allowing conservative amino acid substitution to be generated in an amino acid residue that is not essential to the saccharide oxidase activity. Herein, "conservative amino acid substitution" denotes substitution of an amino acid residue to an amino acid residue having a side chain of the same property. The amino acid residue is classified into some families according to its side chain, for example, the basic side chain (for example, lysin, arginine, and histidine), the acid side chain (for example, asparatic acid, and glutamic acid), the uncharged polar side chain (for example, glycine, asparagine, glutamine, serine, threonine, tyrosine, and cysteine), the nonpolar side chain (for example, alanine, valine, leucine, isoleucine, proline, phenyl alanine, methionine, and tryptophane), β branched side chain (for example, threonine, valine, and isoleucine), and the aromatic side chain (for example, tyrosine, phenyl alanine, tryptophane, and histidine). The conservative amino acid substitution is carried out between the amino acid residues in the same family.

The identity (%) between two amino acid sequences or two nucleic acids (hereinafter, referred to as "two sequences" as a term including the both) can be determined by the following procedure. Firstly, two sequences are aligned for optimum comparison of the two sequences. For example, a gap may be introduced into the first sequence so as to optimize the alignment with respect to the second sequence.

When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain a nucleotide sequence equivalent to the nucleic acid molecule of the present invention, for example, BLAST nucleotide search with score=100 and word length=12 may be carried out by the NBLAST program.

In order to obtain an amino acid sequence equivalent to the polypeptide molecule of the present invention, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used.

Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GEN-ESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. Furthermore, the homology between two nucleic acid sequences can be determined using the GAP program in the GCG software package with the gap weight of 50 and the gap length weight of 3.

The protein according to the present invention may be a part of a larger protein (for example fusion protein). Examples of a sequence to be added in the fusion protein may include a sequence useful for purification, for example, a sequence of a multi histidine residue, and an additional sequence for securing the safety for producing a recombinant, and the like.

The present protein having the aforementioned amino acid sequence can be prepared easily by a gene engineering technique. The present protein having the above-mentioned amino acid sequence can be prepared easily by a genetic engineering technique. For example, the present protein can be prepared by transforming an appropriate host cell (for example, Escherichia coli) by DNA encoding the present protein, and by collecting proteins expressed in the transformant. The collected proteins are appropriately prepared according to the purposes. In the case where the present protein is prepared as a recombinant protein, various modifications can be carried out. For example, DNA encoding the present protein and other appropriate DNA are inserted into the same vector and the vector is used for producing a recombinant protein. Then, the protein consisting of a recombinant protein to which arbitrary peptide or protein is linked can be obtained. Furthermore, modification may be carried out so as to cause addition of sugar chain and/or lipid or processing of N-terminal or C-terminal. The above-mentioned modification permits extraction of a recombinant protein, simplification of preparation, addition of biological functions, or the like.

<2. Gene, Recombinant Vector, and Transformant>
(1) Gene

In the present invention, a gene encoding the aforementioned protein is provided. In one embodiment, the gene of the present invention includes DNA encoding the amino acid sequence set forth in SEQ ID NO: 10. A specific example of this embodiment is a DNA consisting of the base sequence set forth in SEQ. ID. NO:6 or SEQ. ID. NO:9.

In general, when a part of DNA encoding a certain protein is modified, a protein encoded by the modified DNA may sometimes have the equal function to that of a protein encoded by the DNA before modification. That is to say, the modification of the DNA sequence does not have a substantial effect on the function of the encoded protein, so that the function of the encoded protein may be maintained before and after the modification. Thus, as another embodiment, the present invention provides DNA encoding a protein having a base sequence equivalent to the base sequence set forth in SEQ. ID. NO:6 or SEQ. ID. NO:9 and having the saccharide oxidase activity (hereinafter, which is also referred to as "equivalent DNA"). The "equivalent base sequence" herein denotes a base sequence which is partly different from the base sequence set forth in SEQ. ID. NO:6 or SEQ. ID. NO:9 but in which the function (herein, saccharide oxidase activity) of the protein encoded by the sequence is not substantially affected by the difference.

A specific example of the equivalent DNA includes DNA that hybridizes to the complementary base sequence of the base sequence of SEQ. ID. NO:6 or SEQ. ID. NO:9 under stringent conditions. Herein, the "stringent conditions" are referred to as conditions in which a so-called specific hybrid is formed but a nonspecific hybrid is not formed. Such stringent conditions are known to persons skilled in the art. Such stringent conditions can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15 M NaCl, 15 mM sodium citrate, pH 7.0), 5×Denhardt solution, 1% SDS, 10% dextran sulfate, 10 μg/ml denatured salmon sperm DNA, and 50 mM phosphate buffer (pH 7.5)) is used and incubated at about 42° C. to about 50° C., thereafter, washed with 0.1×SSC and 0.1% SDS at about 65° C. to about 70° C. Further preferable stringent conditions can include, for example, a condition in which a hybridization solution 50% formamide, 5×SSC (0.15 M NaCl, 15 mM sodium citrate, pH 7.0), 1×Denhardt solution, 1% SDS, 10% dextran sulfate, 10 μg/ml denatured salmon sperm DNA, and 50 mM phosphate buffer (pH 7.5)) is used.

Another specific example of the equivalent DNA can include DNA encoding a protein having a base sequence which includes substitution, deletion, insertion, addition or inversion in one or a plurality (preferably 1 to several) of bases when the base sequence of SEQ. ID. NO:6 or SEQ. ID. NO:9 is a reference base sequence, and which has a saccharide oxidase activity. The substitution, deletion, or the like, of the base may occur in a plurality of sites. The "plurality" herein denotes, for example, 2 to 40 bases, preferably 2 to 20 bases, and more preferably 2 to 10 bases, although it depends upon the positions or types of the amino acid residue in the three-dimensional structure of the protein encoded by the DNA. The above-mentioned equivalent DNA can be obtained by modifying DNA having the base sequence shown in SEQ. ID. NO:6 or SEQ. ID. NO:9 so as to include substitution, deletion, insertion, addition and/or inversion of base by using treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York) and random mutagenesis (Molecular Cloning, Third Edition, Chapter 13, Cold Spring Harbor Laboratory Press, New York), and the like. Furthermore, the equivalent DNA can be also obtained by other methods such as irradiation with ultraviolet ray.

A further example of the equivalent DNA can include DNA having difference in base as mentioned above due to polymorphism represented by SNP (single nucleotide polymorphism).

The gene of the present invention can be prepared in an isolated state by using a standard genetic engineering technique, a molecular biological technique, a biochemical technique, and the like, with reference to sequence information disclosed in the present specification or attached sequence list. Specifically, the gene of the present invention can be prepared by appropriately using oligonucleotide probe/primer capable of specifically hybridizing to the gene of the present invention from an appropriate genome DNA library or a cDNA library of *Acremonium chrysogenum*, or cell body extract of *Acremonium chrysogenum*. An oligonucleotide probe/primer can be easily synthesized by using, for example, a commercially available automated DNA synthesizer. As to a production method of libraries used for preparing the gene of the present invention, see, for example, Molecular Cloning, Third Edition, Cold Spring Harbor Laboratory Press, New York.

For example, a gene having the base sequence set forth in SEQ. ID. NO:6 or SEQ. ID. NO:9 can be isolated by using a hybridization method using all or a part of the base sequence or its complimentary sequence as a probe. Furthermore, amplification and isolation can be carried out by using a nucleic acid amplification reaction (for example, PCR) using a synthesized oligonucleotide primer designed to specifically hybridize to a part of the base sequence. Furthermore, it is possible to obtain a target gene by chemical synthesis based on the information of the amino acid sequence set forth in SEQ ID NO: 10 or the base sequence set forth in SEQ. ID. NO:6 or SEQ. ID. NO:9 (see, reference document: Gene, 60(1), 115-127 (1987)).

Hereinafter, a specific example of the method of obtaining the gene of the present invention is described. Firstly, the present enzyme (saccharide oxidase) is isolated and purified from *Acremonium chrysogenum*, and information about the partial amino acid sequence is obtained. As a method for determining the partial amino acid sequence thereof, for example, purified β-amylase is directly subjected to amino acid sequence analysis [protein-sequencer 476A, Applied Biosystems] by Edman Degradation [Journal of biological chemistry, vol. 256, pages 7990-7997 (1981)] according to a routine method. It is effective that limited hydrolysis is carried out by allowing protein hydrolase to act, the obtained peptide fragment is separated and purified, and the thus obtained purified peptide fragment is subjected to the amino acid sequence analysis.

Based on the information of thus obtained partial amino acid sequence, a saccharide oxidase gene is cloned. Cloning can be carried out by using, for example, a hybridization method or a PCR method. When the hybridization method is used, for example, a method described in Molecular Cloning (Third Edition, Cold Spring Harbor Laboratory Press, New York) can be used.

When the PCR method is used, the following method can be used. Firstly, PCR reaction is carried out by using a synthesized oligonucleotide primer designed based on the information of the partial amino acid sequence using a genome DNA of a microorganism producing saccharide oxidase as a template, and thus a target gene fragment is obtained. The PCR method is carried out according to the method described in PCR Technology, edited by Erlich. H A, Stocktonpress, 1989]. Furthermore, when a base sequence is determined by a method usually used in the amplification DNA fragment, for example, a dideoxy chain terminator method, a sequence corresponding to the partial amino acid sequence of saccharide oxidase other than the sequence of the synthesized oligonucleotide primer is found in the determined sequence, and a part of the saccharide oxidase gene can be obtained. When a hybridization method and the like is further carried out by using the obtained gene fragment as a probe, a gene encoding the full length of the saccharide oxidase can be cloned.

In the below mentioned Examples, a sequence of a gene encoding saccharide oxidase produced by *Acremonium chrysogenum* is determined by using the PCR method. The complete base sequence of a gene encoding saccharide oxidase produced by *Acremonium chrysogenum* is shown in SEQ ID NO: 6, and the complete base sequence of the cDNA which encodes this enzyme is represented in SEQ. ID. NO:9. Furthermore, the amino acid sequence encoded by the base sequence is determined (SEQ ID NO: 10). In addition to the base sequence shown in SEQ. ID. NO:6 or SEQ. ID. NO:9, a plurality of the base sequences corresponding to the amino acid sequence set forth in SEQ ID NO: 10 are present.

All or a part of the saccharide oxidase gene (SEQ ID NO: 6) whose complete base sequence has been clarified is used as a probe of hybridization, and thereby DNA having high homology with respect to the saccharide oxidase gene of SEQ. ID. NO:6 or SEQ. ID. NO:9 can be selected from a genome DNA library or a cDNA library of microorganisms producing other saccharide oxidase.

Similarly, a primer for PCR can be designed. By carrying out PCR reaction using this primer, a gene fragment having high homology with respect to the above-mentioned saccharide oxidase gene can be detected and, furthermore, a complete gene thereof can be obtained.

Protein of the obtained gene is manufactured, and its saccharide oxidase activity is measured. Thereby, it is possible to confirm whether or not the obtained gene is a gene encoding a protein having the saccharide oxidase activity. Furthermore, by comparing the base sequence (or the amino acid sequence encoded thereby) of the obtained gene with the base sequence (or the amino acid sequence encoded thereby) of the above-mentioned saccharide oxidase gene, the gene structure or the homology may be examined, thereby determining whether or not the gene encodes protein having the saccharide oxidase activity.

Since the primary structure and the gene structure are clarified, modified saccharide oxidase (a gene subjected to at least one of deletion, addition, insertion, and substitution of one or a plurality of amino acid residues) can be obtained by introduction of random mutation or site-specific mutation. This makes it possible to obtain a gene encoding saccharide oxidase that has a saccharide oxidase activity but has different optimum temperature, thermostability, optimum pH, stable pH, substrate specificity, and the like. Furthermore, it becomes possible to manufacture modified saccharide oxidase by genetic engineering.

Herein, a scheme for introducing mutation is carried out with consideration of, for example, a characteristic sequence of a gene sequence. The consideration of a characteristic sequence can be made by considering, for example, the prediction of the three-dimensional structure of the protein, and homology to existing proteins.

Examples of the method for introducing random mutation include: a method, as method of chemically treating DNA, which causes transition mutation in which sodium hydrogensulfite is allowed to act and cytosine base is converted into uracil base [Proc. Natl. Acad. Sci. U.S.A., 79, 1408-1412 (1982)]; a method, as a biochemical method, which causes base substitution during the process of synthesizing the double strand in the presence of [α-S]dNTP [Gene, vol 64, pages 313-319 (1988)]; a method, as a method of using PCR, which carries out PCR in a reaction system with manganese added, thereby lowering fidelity of incorporation of nucleotides [Anal. Biochem., 224, 347-353 (1995)], and the like.

Examples of the method for introducing site-specific mutation include a method using amber mutation [gapped duplex method; Nucleic Acids Res., Vol. 12, No. 24, 9441-9456 (1984)]; a method using a recognition site of the restriction enzyme [Analytical Biochemistry, Vol. 200, pages 81-88 (1992), Gene, Vol. 102, pages 67-70 (1991)]; a method using mutation of dut (dUTPase) and ung (uracil-DNA glycosilase) [Kunkel method; Proc. Natl. Acad. Sci. U.S.A., 82, 488-492 (1985)]; a method using amber mutation using DNA polymerase and DNA ligase [Oligonucleotide-directed Dual Amber: ODA) method, Gene, Vol. 152, pages 271-275 (1995), Japanese Patent Application Unexamined Publication No. H7-289262]; a method using a host inducing a repair system of DNA (Japanese Patent Application Unexamined Publication No. H8-70874); a method using a protein catalyzing a DNA strand exchange reaction (Japanese Patent Application Unexamined Publication No. H8-140685); a method by PCR using two types of primers for introducing a restriction enzyme into which the recognition site is added (U.S. Pat. No. 5,512,463); a method by PCP using a double strand DNA vector having inactivated drug-resistant gene and two types of primers [Gene, Vol. 103, pages 73-77 (1991)]; a method by PCR using amber mutation [International Publication WO98/02535], and the like.

Otherwise, the site-specific mutation can be easily introduced by using commercially available kits. Examples of the commercially available kits include Mutan-G (register trade mark, Takara Shuzo Co., Ltd.) using the gapped duplex method, Mutan-K (register trade mark, Takara Shuzo Co., Ltd.) using the Kunkel method, Mutan-ExpressKm (register trade mark, Takara Shuzo Co., Ltd.) using the ODA method, QuikChange™ Site-Directed Mutagenesis Kit [STRATAGENE] using a primer for introducing mutation and DNA polymerase derived from *Pyrococcus furiosus*, and the like. Furthermore, as the kits using the PCR method, for example, TaKaRa LA PCR in vitro Mutagenesis Kit (Takara Shuzo Co., Ltd.), Mutan (register trade mark)—Super Express Km (Takara Shuzo Co., Ltd.), and the like.

Thus, the primary structure and the gene structure of saccharide oxidase are provided by the present invention. As a result, it is possible to genetically manufacture proteins having a saccharide oxidase activity with high purity at low cost.

(2) Recombinant Vector

The gene according to the present invention can be used as being inserted into a appropriate vector. The type of the vector which can be used in the present invention is intended to refer to a nucleic acid molecule capable of transporting nucleic acid that is inserted in the vector to the inside of the target such as cells. The types or forms of vector are not particularly limited. Therefor, examples of the vector may be in a form of a plasmid vector, a cosmid vector, a phage vector, a viral vector (e.g., an adenovirus vector, an adeno-associated virus vector, a retrovirus vector, a herpes virus vector, etc).

According to the purpose of use (cloning, protein expression), and by considering the types of host cells, an appropriate vector is selected. Specific examples of the vector include a vector using *Escherichia coli* as a host (M13 phage or the modified body thereof, λ phage or the modified body thereof, pBR322 or the modified body thereof (pB325, pAT153, pUC8, etc.) and the like), a vector using yeast as a host (pYepSec1, pMFa, pYES2, etc.), a vector using insect cells as a host (pAc, pVL, etc.), a vector using mammalian cells as a host (pCDM8, pMT2PC, etc.), and the like.

The recombinant vector of the present invention is preferably an expression vector. The term "expression vector" is a vector capable of introducing the nucleic acid inserted therein into the target cells (host cells) and being expressed in the cells. The expression vector usually includes a promoter sequence necessary for expression of the inserted nucleic acid and an enhancer sequence for promoting the expression, and the like. An expression vector including a selection marker can be used. When such an expression vector is used, by using the selection marker, the presence or absence of the introduction of an expression vector (and the degree thereof) can be confirmed.

Insertion of the gene of the present invention into a vector, insertion of the selection marker gene (if necessary), and insertion of a promoter (if necessary), and the like, can be carried out by a standard recombination DNA technology (see, for example, Molecular Cloning, Third Edition, 1.84, Cold Spring Harbor Laboratory Press, New York, a already-known method using restriction enzyme and DNA ligase).

(3) Transformant

By transducing the recombinant vector of the present invention into an appropriate host, a transformant can be prepared. In the transformant of the present invention, the gene of the present invention exists as an exogenous molecule. Preferably, the transformant of the present invention can be preferably prepared by transfection or transformation using the vector of the present invention mentioned above. The transfection and transformation can be carried out by, for example, a calcium phosphate coprecipitation method, electroporation (Potter, H. et al., Proc. Natl. Acad. Sci. U.S.A. 81, 7161-7165(1984)), lipofection (Feigner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73, 366-370 (1976)), a method by Hanahan (Hanahan, D., J. Mol. Biol. 166, 557-580 (1983)), a lithium acetate method (Schiestl, R. H. et al., Curr. Genet. 16, 339-346 (1989)), protoplast—polyethylene glycol method (Yelton, M. M. et al., Proc. Natl. Acad. Sci. 81, 1470-1474 (1984)), and the like.

The host cell is not limited particularly as long as it allows the saccharide oxidase of the invention to be expressed, and may for example be bacteria of genus *Bacillus* such as *Bacillus subtilis, Bacillus licheniformis*, and *Bacillus circulans*, bacteria of genus *Lactobacillus* such as *Lactococcus, Lactobacillus, Streptococcus, Leuconostoc*, and *Bifidobacterium*, other bacteria such as *Escherichia* and *Streptomyces*, yeast such as *Saccharomyces, Kluyveromyces, Candida, Torula*, and *Torulopsis*, microorganisms of genus *Aspergillus* such as *Aspergillus oryzae* and *Aspergillus niger*, mycotic microorganism (fungi) of genus *Penicillium*, genus *Trichoderma*, genus *Fusarium*, and the like. As the animal cell, baculovirus may be used.

<3. Manufacturing Method of Protein Having Saccharide Oxidase Activity>

The method of producing the protein having a saccharide oxidase activity according to the present invention is not limited particularly, and any known method can be used. Typically, the protein according to the present invention can be produced by collecting a protein having a saccharide oxidase activity from a culture obtained by culturing a microorganism having an ability of producing the protein according to the present invention or a transformant according to the present invention in a nutrient medium.

The microorganism which can be used in the production method according to the present invention is not limited particularly as long as it is a microorganism having the aforementioned physicochemical characteristics and an ability of producing a protein having a saccharide oxidase activity, and any known microorganism can be selected and used. For example, microorganisms belonging to genus *Acremonium* can be exemplified. In such a case, the microorganism belonging to genus *Acremonium* may for example be *Acremonium chrysogenum*.

In addition, the aforementioned microorganism used in the production method according to the present invention is not limited to the wild-type strain and any mutant obtained from the aforementioned wild-type strain by an artificial variation means using ultraviolet, x-ray, radiation, various reagents, and the like can be used as long as it has an ability of producing an enzyme having the aforementioned saccharide oxidase activity.

The culture in the production method according to the present invention may employ any appropriate known technique, and any liquid culture and solid culture may for example be used.

In the culture in the production method according to the present invention, the carbon source of the culture medium which can be used is not limited particularly, and any one or more carbon sources used in known culture medium can be selected and used. For example, those which may exemplified are glucose, fructose, sucrose, lactose, starch, glycerin, dextrin, lecithin, and the like.

Similarly, the nitrogen source is not limited particularly, and any one or more nitrogen sources used in known culture medium can be selected and used. For example, any of inorganic nitrogen sources such as ammonium sulfate, ammonium nitrate, diammonium hydrogen phosphate, ammonium dihydrogen phosphate, ammonium chloride, and the like, as well as organic nitrogen sources such as corn gluten meal, soybean meal, casamino acid, coffee grounds, cottonseed oil cake, yeast extract, malt extract, corn steep liquor, casein hydrolysate, bran, meet extract, amino acid, peptone, and the like can be used.

Also similarly, the mineral nutrition source is not limited particularly, and any one or more mineral nutrition sources used in known culture medium can be selected and used. For example, sodium, magnesium, potassium, iron, zinc, calcium, and manganese salts as well as vitamins are exemplified.

The typical temperature at which the culture is conducted in the production method of the present invention is not limited particularly, and any temperature can be used as long as the effect of the present invention is not affected adversely. In the present invention, a temperature within a range from 20 to 35° C. is preferred, and a temperature within a range from 25 to 30° C. is more preferred.

Similarly, the pH of the culture medium is not limited particularly, and any pH can be used as long as the effect of the present invention is not affected adversely. In the present invention, a pH of 5 to 8 is preferred, and a pH of 6 to 7 is more preferred.

Similarly, the culture period in the production method according to the present invention is not limited particularly, and any time period can be employed depending on the cell density, pH of the culture medium, temperature of the culture medium, composition of the culture medium, and the like, as long as the effect of the present invention is not affected adversely. In the present invention, a culture period is preferably 3 to 8 days, and more preferably 4 to 7 days. The mode of the culture may be a static culture, shaking culture, aerobic deep culture using a jar fermenter, and the like.

After culturing the cell as described above, the protein of the present invention is purified and recovered. The method for purifying and recovering the protein is not limited particularly, and any known method can be selected and used.

For example, recovery from a culture fluid is accomplished by filtration of the culture supernatant and centrifugation to remove insolubles followed by separation and purification using an appropriate combination of concentration through an ultrafiltration membrane, salting out such as ammonium sulfate precipitation, dialysis, and various chromatographies such as ion exchange resin, thereby obtaining the present protein.

On the other hand, recovery from the inside of cells is accomplished by pressurization or ultrasonication to crush the cells followed by separation and purification as described above, thereby obtaining the present protein. It is also possible that the cells are recovered preliminarily from the culture fluid by filtration, centrifugation, and the like and thereafter the aforementioned series of processes (cell crushing, separation, and purification) are conducted.

While it is convenient to verify the expression or to verify the expression product using an antibody to the saccharide oxidase, it is also possible to verify the expression by measuring the saccharide oxidase activity.

In another embodiment of the present invention, the aforementioned transformant is used to produce the saccharide oxidase. In the production method of this embodiment, the aforementioned transformant is cultured under a condition which enables the production of the protein encoded by the gene which was introduced into it. The conditions of the culture of the transformants are known for various vector-host systems, and an appropriate culture condition can readily be established by those skilled in the art. Following the culture step, the produced protein (i.e., saccharide oxidase) is recovered. The recovery and subsequent purification may be conducted as in the aforementioned embodiment.

<4. Use and Application of Protein According to Present Invention>

While the protein of the present invention can be used in the form which is not limited particularly, it can be provided for example in the form of an enzyme preparation. The enzyme preparation may contain any one or more pharmaceutically acceptable additives in addition to the active ingredient (the protein of the present invention). For example, those which may be contained are excipients, buffers, suspending agents, stabilizers, preservatives, antiseptics, physiological saline, and the like. Those which may be used as excipients include starch, dextrin, maltose, trehalose, lactose, D-glucose, sorbitol, D-mannitol, sugar, glycerol, and the like. Those which may be used as buffers include phosphates, citrates, acetates, and the like. Those which may be used as stabilizers include propylene glycol, ascorbic acid, and the like. Those which may be used as preservatives include phenol, benzalkonium chloride, benzyl alcohol, chlorobutanol, methyl paraben, and the like. Those which may be used as antiseptics include ethanol, benzalkonium chloride, p-oxybenzoic acid, chlorobutanol, and the like.

By using the protein according to the present invention to oxidize the saccharide capable of serving as a substrate described above, a saccharic acid can be produced. The protein according to the present invention can function as a saccharide oxidase in any field as long as the saccharide capable of serving as a substrate described above exists. Especially since the protein according to the present invention has a property which is an ability of acting on a wide range of saccharides, it can preferably be used when it is required to oxidize a multiple number of saccharide at once. Also since the protein according to the present invention has a suitable degree of the thermostability, it can preferably be used when a saccharide is oxidized to a saccharic acid whose enzymatic activity should thereafter be inactivated.

A typical example is to use preferably for oxidizing a saccharide in a food product. Such a use can be applied for various purposes. For example, the use can be made preferably in (1) a method for desugaring egg white and a method for producing desugared egg white, (2) a method for modifying the quality of a bread and/or the physical property of a dough and method for producing bread, (3) a method for producing lactobionic acid, and the like.

(1) Method for Desugaring Egg White and Method for Producing Desugared Egg White The protein according to the present invention can be used preferably for desugared egg white.

A saccharide contained in the egg white, such as glucose, causes problematic coloration due to Maillard reaction upon production, for example, of a confectionery. Accordingly, the desugared egg white has conventionally been used in producing confectioneries and the like.

Those which have conventionally been used for desugaring the egg white are treatment with a glucose oxidase and fermentation using yeast. Nevertheless, the treatment with the glucose oxidase problematically allows the activity to remain in the desugared egg white because of a relatively high thermostability. The glucose oxidase whose activity remains has been serve to oxidize the glucose contained for example in the raw material of a confectionery, resulting in a problematic reduction in the sweetness. On the other hand, the fermentation method imparts a problematic fermentation odor to the egg white after desugaring treatment, resulting in a problematic limitation in using the egg white.

Also since the protein according to the present invention has a thermostability which is not too high but is appropriate, the activity characteristically tends to be reduced in the egg white once desugared. Accordingly, the problematic reduction in the sweetness of the final food product due to the residual activity can be improved.

Moreover, since the desugaring method using the protein according to the present invention is a method for changing a saccharide in the egg white into a saccharic acid which is different from a fermentation method, a problem due to the fermentation odor can also be solved.

(2) Method for Modifying Quality of Bread and/or Physical Property of Dough and Method for Producing Bread The protein according to the present invention can be preferably used for modifying the quality of bread and/or the physical property of dough.

Typically, a saccharide contained in a raw material used in bread-making is oxidized to produce hydrogen peroxide which serves for tightening the unbaked preparation of bread (dough) and reducing the stickiness in the production process, thereby enabling an easy handling and an improved physical property.

Conventionally, the physical property of the unbaked preparation of bread (dough) has been improved by adding a saccharide oxidase to wheat flour. Typically, a glucose oxidase is used alone or in combination with other enzymes in producing breads while expecting an effect to tighten the unbaked preparation of bread (dough). Nevertheless, since wheat flour generally has a glucose level within the range from 0 to 0.4% by weight, it is difficult to improve the quality actually only by the glucose oxidase, and it is required to use other enzyme at the same time.

On the other hand, since the protein according to the present invention acts on a wide range of saccharides in addition to the glucose, an excellent modifying effect on the quality of bread or on the physical property of dough can be exerted only by the protein according to the present invention.

(3) Method for Producing Lactobionic Acid

Since the protein according to the present invention acts also on lactose, it can preferably be used in a method for producing lactobionic acid by oxidizing lactose.

The lactobionic acid is known to form a salt with an inorganic cation such as calcium, potassium, sodium, zinc, and the like, thereby promoting the absorption of minerals. In addition, the lactobionic acid is used as an antioxidant in the field of cosmetics and calcium lactobionate is used widely as a stabilizer in the field of food products. Accordingly, the protein according to the present invention can preferably be used also for producing the lactobionic acid which is used in a wide range of the fields.

Conventionally the lactobionic acid has been subjected to the method in which milk is inoculated with an *Acetobacter* microorganism to effect fermentation to convert the lactose in the milk into the lactobionic acid.

Nevertheless, by using the protein according to the present invention, the production of the lactobionic acid by an enzymatic method becomes possible.

EXAMPLES

Hereinafter, the present invention is described in further detail based on Examples while verifying the effects of the invention. The Examples described below shows merely the representatives of the present invention, by which the scope of the present invention is not interpreted narrowly.

Unless otherwise specified, the saccharide oxidase activity was measured by the following method in these Examples.

<Saccharide Oxidase Activity Measuring Method>

2 ml of 0.1M monopotassium phosphate-sodium hydroxide buffer solution (pH7.0) containing 0.15% (W/V) phenol and 0.15% (WN) TritonX-100, 0.5 mL of 10% maltose monohydrate, 0.5 ml of 25 U/mL peroxidase solution, and 0.1 ml of 0.4% (W/V) 4-aminoantipyrine solution were mixed, kept at 37° C. for 10 minutes, and then 0.1 ml of the enzyme solution was added to initiate the reaction. Since a quinoneimine color having absorption band at a wavelength of 550 nm was formed when the enzymatic reaction advanced, the saccharide oxidase activity was measured by measuring the increase in the absorbance at a wavelength of 550 nm per minute. The quantity of the enzyme required to oxidize 1 µmol of maltose monohydrate per minute was regarded as 1 unit.

Example 1: Production and Purification of Protein Having a Saccharide Oxidase Activity In Example 1, a protein having a saccharide oxidase activity according to the present invention was purified. In the following Examples, as an example of the microorganism having an ability of producing the protein according to the present invention, a microorganism belonging to genus *Acremonium*, namely, *Acremonium chrysogenum* was used.

(1) Culture

Three strains of *Acremonium chrysogenum*, namely, NBRC30055, ATCC15006, and DSM880 were subjected to a pre-culture and then subjected to a shaking culture for 6 days at 30° C. using a liquid medium having the composition indicated in Table 1 shown below. After the culture, the culture fluid was filtered through the filter paper No. 2 (manufactured by Advantec Toyo Kaisha, Ltd.) to recover the culture filtrate. The saccharide oxidase activity of the culture filtrate obtained was measured by the aforementioned saccharide oxidase activity measuring method. The results are shown in Table 2.

TABLE 1

Saccharide oxidase production medium

|  | (W/V) |
| --- | --- |
| Corn steep liquor | 3.0% |
| D-Glucose | 1.0% |
| Soluble starch | 3.0% |
| Calcium carbonate | 0.5% |

TABLE 2

|  | Activity (U/ml) |
| --- | --- |
| NBRC30055 | 0.014 U/ml |
| ATCC15006 | 0.014 U/ml |
| DSM880 | 0.012 U/ml |

(2) Purification of *Acremonium chrysogenum* NBRC30055-Derived Saccharide Oxidase The culture filtrate obtained as described above was filtered through a diatomaceous earth using Radiolite Fine Flow A (manufactured by Showa Chemical Industry Co., Ltd.), and then concentrated by an UF membrane (AIP-1013D, manufactured by Asahi Kasei Corporation), combined with ammonium sulfate at a concentration of 65% saturation, and the resultant supernatant was combined with ammonium sulfate at a concentration of 90% saturation. The resultant precipitation fraction was dissolved in 2M ammonium sulfate-containing 20 mM Tris-HCl buffer solution (pH8.0). A HiLoad 16/10 Phenyl Sepharose HP column (manufactured by GE Healthcare) equilibrated with 2M ammonium sulfate-containing 20 mM Tris-HCl buffer solution (pH8.0) was used to elute the absorbed saccharide oxidase protein using a linear gradient of 2M to 0M of ammonium sulfate.

The collected saccharide oxidase fraction was concentrated through an UF membrane, and then dialyzed against 20 mM Tris-HCl buffer solution (pH7.4) containing 1 mM manganese chloride, 1 mM potassium chloride, and 0.5M sodium chloride. The resultant intradialysis solution was subjected to a HiTrap ConA 4B column (manufactured by GE Healthcare) equilibrated with 20 mM Tris-HCl buffer solution (pH7.4) containing 1 mM manganese chloride, 1 mM potassium chloride, and 0.5M sodium chloride, and subjected to a stepwise elution with 20 mM Tris-HCl buffer solution (pH7.4) containing 0.5M Methyl-α-D-glucopyranoside (MDGP) and 0.5M sodium chloride thereby eluting the absorbed saccharide oxidase protein.

The collected saccharide oxidase fraction was concentrated through an UF membrane, and then dialyzed against 20 mM monopotassium phosphate-sodium hydroxide buffer solution (pH6.0) and the intradialysis solution was subjected to a Mono Q HR 5/5 column (manufactured by GE Healthcare) equilibrated with 20 mM monopotassium phosphate-sodium hydroxide buffer solution (pH6.0), and then the absorbed saccharide oxidase protein was eluted using a linear gradient of sodium chloride from 0M to 1M.

Furthermore, the collected saccharide oxidase fraction was concentrated through an UF membrane, and then dialyzed against a 0.3M sodium chloride-containing 25 mM Tris-HCl buffer solution (pH8.0), and the resultant intradialysis solution was subjected to a HiLoad 16/60 Superdex 200 μg column (manufactured by GE Healthcare) equilibrated with 0.3M sodium chloride-containing 25 mM Tris-HCl buffer solution (pH8.0), and eluted with the same buffer solution. The saccharide oxidase protein was collected and desalted and concentrated using an ultrafiltration membrane to obtain a purified enzyme preparation. This purified enzyme thus obtained was subjected to the investigation for the following various natures, and also analyzed for the peptide amino acid sequence for the internal peptide.

The results of the purification in each stage are indicated in Table 3 shown below. The specific activity of the final stage was about 160 times that of the crude enzyme. FIG. 1 shows the results of the 10% gel SDS-PAGE (silver staining) of the sample in the final purification process.

TABLE 3

|  | Total protein (mg) | Total activity (U) | Specific activity (U/mg) | Recovery (%) |
| --- | --- | --- | --- | --- |
| Concentrate | 2765 | 49 | 0.018 | 100% |
| Ammonium sulfate fractionation | 1807 | 41 | 0.023 | 84% |
| Phenyl HP | 538 | 35 | 0.064 | 71% |
| ConA 4B | 76 | 19 | 0.246 | 39% |
| Mono Q HR | 30 | 16 | 0.55 | 33% |
| Superdex 200 | 3 | 8 | 2.9 | 16% |

Example 2: Investigation of Substrate Specificity

In Example 2, the substrate specificity to each substrate was investigated.

Using each saccharide indicated in Table 4 shown below as a substrate and in the presence of oxygen, the protein purified in Example 1 described above was reacted for 5 minutes at 37° C. at pH 7.0, and the measurement was conducted in accordance with the aforementioned saccharide oxidase activity measuring method. In addition, regarding the activity toward the glucose as 100%, the relative value of the activity toward each saccharide was calculated, thereby evaluating the substrate specificity. The results are indicated in Table 4 shown below.

TABLE 4

| Substrate | Relative activity (%) |
| --- | --- |
| Glucose | 100% |
| Maltose monohydrate | 86% |
| Maltotriose | 92% |
| Maltotetraose | 60% |
| Maltopentaose | 39% |
| Maltohexaose | 28% |
| Maltoheptaose | 24% |
| Galactose | 79% |
| Lactose monohydrate | 58% |

TABLE 4-continued

| Substrate | Relative activity (%) |
| --- | --- |
| D(+)-Cellobiose | 53% |
| D(−)-Fructose | 0% |
| Sucrose | 0% |
| Pinedex #2 (Trade mark) | 24% |

As shown in Table 4, a satisfactory effect was observed on glucose, maltose monohydrate, maltotriose, maltotetraose, galactose, lactose monohydrate and D(+)-cellobiose. No effect was observed on D(−)-fructose or sucrose.

Example 3: Investigation of Optimum pH

Figure 2:
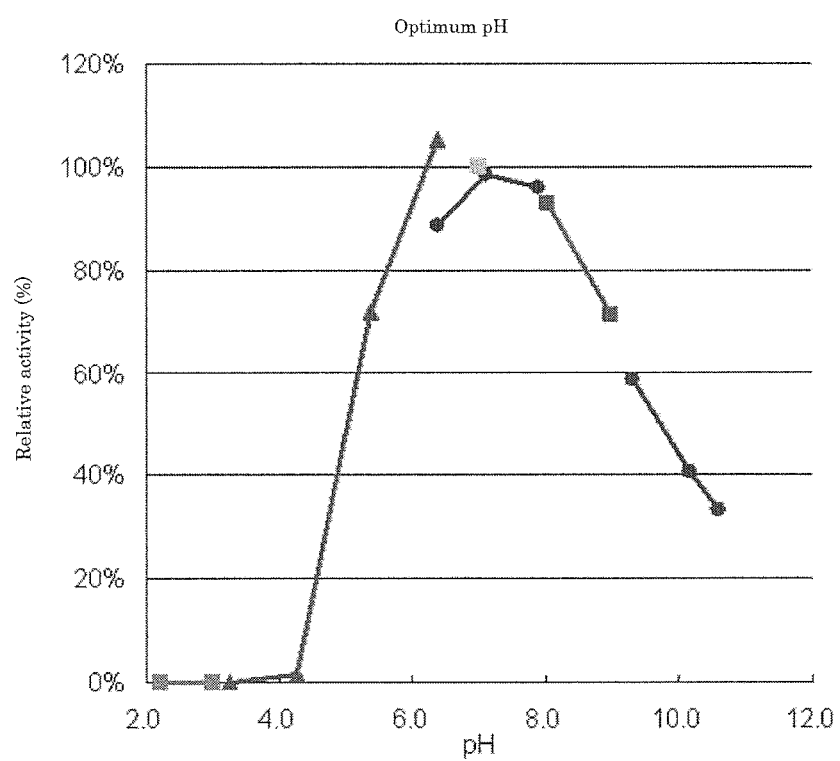
FIG. 2 is a drawing-substituting graph exhibiting the relative activity (%) versus pH in Example 3.

In accordance with the aforementooned saccharide oxidase activity measuring method, in the respective buffer solutions (glycine-HCl buffer solution (pH2.0, pH3.0), citric acid-sodium citrate buffer solution (pH3.0, pH4.0, pH5.0, pH6.0), monopotassium phosphate-dipotassium phosphate buffer solution (pH6.0, pH7.0, pH8.0), Tris-HCl buffer solution (pH8.0, pH9.0), sodium carbonate-sodium hydrogen carbonate buffer solution (pH9.0, pH10.0, pH11.0) and monopotassium phosphate-sodium hydroxide buffer solution (pH7.0)), measurement was conducted under the reaction condition involving 37° C. for 5 minutes. In addition, regarding the activity when using monopotassium phosphate-sodium hydroxide buffer solution (pH7.0) as 100%, each relative value of the activity was calculated. The results are indicated in the drawing-substituting graph of FIG. 2. The optimum pH was 5.0 to 9.0.

Example 4: Investigation of pH Stabiliry

Figure 3:
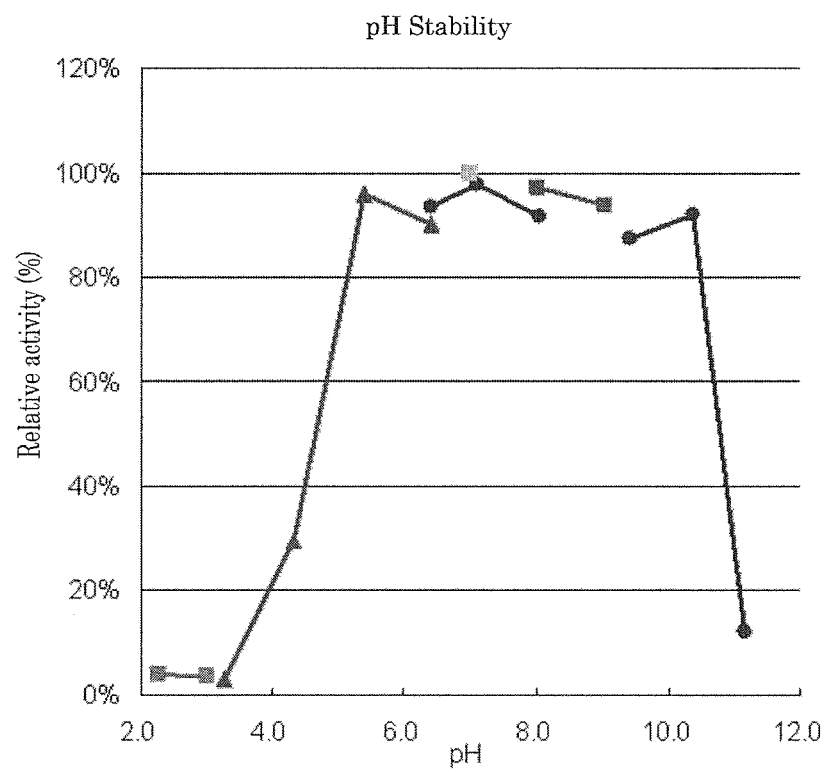
FIG. 3 is a drawing-substituting graph exhibiting the relative activity (%) versus pH in Example 4.

The protein solution purified in the aforementioned Example 1 and the buffer solution of each pH used in the aforementioned Example 3 were mixed in equal volumes and treated for 15 minutes at 37° C., and thereafter the activity was measured by the aforementioned saccharide oxidase activity measuring method. As a substrate, maltose was used. In addition, regarding the activity when using monopotassium phosphate-sodium hydroxide buffer solution (pH7.0) for treatment as 100%, each relative value of the activity was calculated. The results are indicated in the drawing-substituting graph of FIG. 3. The residual activity was 85% or higher at a pH within the range from pH5.0 to pH10.5, and stability was observed at a pH within the range from pH5.0 to pH10.5.

Example 5: Investigation of Optimum Temperature

Figure 4:
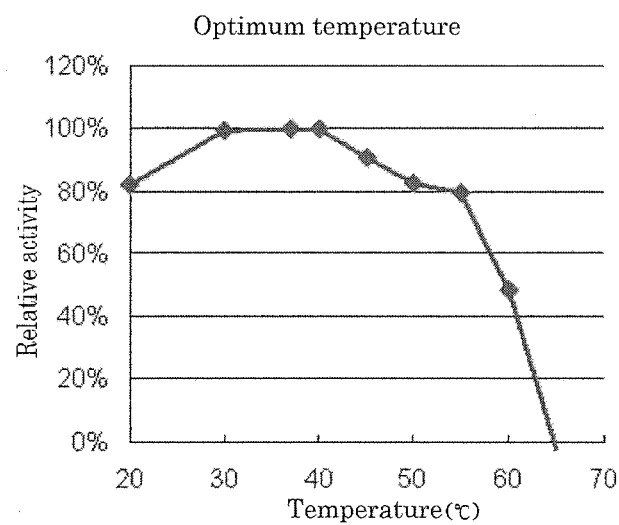
FIG. 4 is a drawing-substituting graph exhibiting the relative activity (%) versus temperature in Example 5.

Using maltose as a substrate and in the presence of oxygen, the protein purified in the aforementioned Example 1 was reacted at pH7.0 and at a reaction temperature of 20° C., 30° C., 37° C., 40° C., 45° C., 50° C., 55° C., 60° C., and 65° C. for 5 minutes, thereby producing hydrogen peroxide. The hydrogen peroxide thus produced was reacted with a peroxidase in the presence of aminoantipyrine, TOOS (manufactured by Dojindo Laboratories) and the color tone exhibited by the quinoneimine color produced was measured at a wavelength of 555 nm, thereby accomplish quantification. In addition, regarding the activity at a reaction temperature of 37° C. as 100%, each relative value of the activity was calculated. The results are indicated in the drawing-substituting graph of FIG. 4. The optimum temperature was 20° C. to 55° C.

Example 6: Investigation of Thermostability

Figure 5:
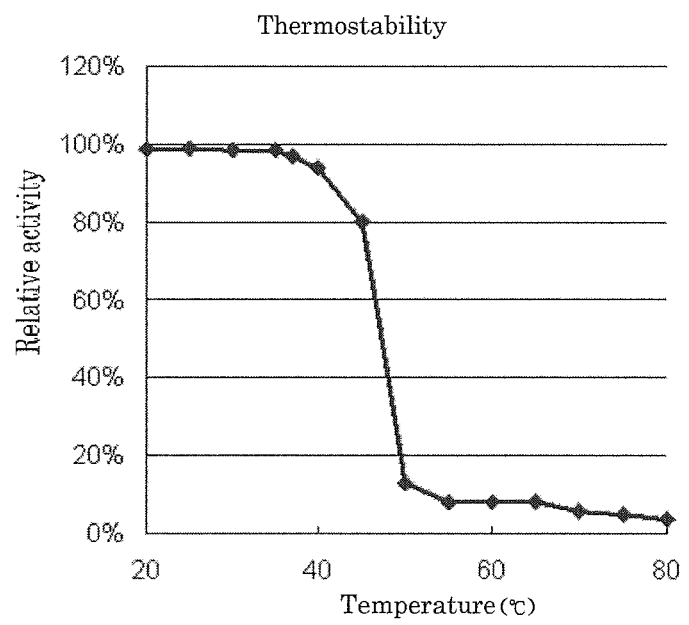
FIG. 5 is a drawing-substituting graph exhibiting the relative activity (%) versus temperature in Example 6.

The protein solution purified in the aforementioned Example 1 was subjected to a heat treatment for 15 minutes at a temperature of 20° C., 25° C., 30° C., 35° C., 37° C., 40° C., 45° C., 50° C., 55° C., 60° C., 65° C., 70° C., 75° C., and 80° C., and thereafter the residual activity was measured by the aforementioned saccharide oxidase activity method. Regarding the activity with no heat treatment as 100%, each value of the residual activity was calculated. The results are indicated in the drawing-substituting graph of FIG. 5. There was a residual activity of 80% or higher with a heat treatment for 15 minutes at 45° C., and the stability was observed at a temperature up to 45° C.

Example 7: Measurement of Molecular Weight

The protein purified in the aforementioned Example 1 was subjected to an SDS-PAGE method to calculate the molecular weight, which was found to be about 63 kDa.

Example 8: Measurement of Km Value

Using the protein purified in the aforementioned Example together with glucose and maltose as substrates, the aforementioned saccharide oxidase activity method was used to measure the activity thereby obtaining Hanes-Woolf plots, from which each Michaelis constant (Km) was obtained. As a result, it was found that the Km value for glucose was 8 mM, and the Km value for maltose was 14 mM.

Example 9: Desugaring of Egg White

In Example 9, the protein purified in the aforementioned Example 1 and a glucose oxidase ("Hyderase 15" manufactured by Amano Enzyme Inc.) were used to desugaring egg white.

(1) Preparation of Egg White

Egg yolk and egg white were separated, and the water-soluble egg white and the thick egg white were mixed using a whisk to the extent of no foaming, and dispensed in 20 mL aliquots into 100-mL flasks using a volumetric pipette. Each 100-mL flask thus dispensed received a stirring bar and agitated vigorously using a water-bath-fitted stirrer, thereby preparing egg white.

(2) Desugaring Reaction of Egg White

The egg white prepared as described above was combined with 6 U or 15 U of the protein purified in the aforementioned Example 1 and 6 U or 15 U of the glucose oxidase, sealed with an aluminum foil for avoiding any evaporation of water, then the reaction was initiated.

Before addition of the enzyme, and every 1 hour for 1 to 5 hours after initiation of the reaction, 500 µL was sampled. Thereafter, the reaction was quenched by freezing at −30° C.

(3) Measurement of Residual Glucose Amount

Each egg white sampled as described above was examined for its residual glucose amount. For measurement of the glucose amount, α-D-glucose in the treated egg white solution was converted into β-D-glucose by a mutarotase and then converted into D-glucono-1,5-lacton by a glucose dehydrogenase in the presence of β-NAD+. During this course, β-NADH+ formed was measured at a wavelength of 340 nm to accomplish quantification.

Typically, to 3.4 mL of 100 mM BES buffer solution (pH7.0) containing 1 mM EDTA, 0.05% sodium azide, 0.14% TritonX-100, 0.8 mM β-NAD+, 2 U/ml MUT "AMANO" II (manufactured by Amano Enzyme Inc.), and 14 U/ml GLUCDH "AMANO" II (manufactured by Amano Enzyme Inc.), 76 μL of the treated egg white solution which had been diluted appropriately was added, and the mixture was incubated at 37° C. for 10 minutes. After incubation, the absorbance at a wavelength of 340 nm was measured to quantify the residual glucose amount.

(4) Results

Figure 6:
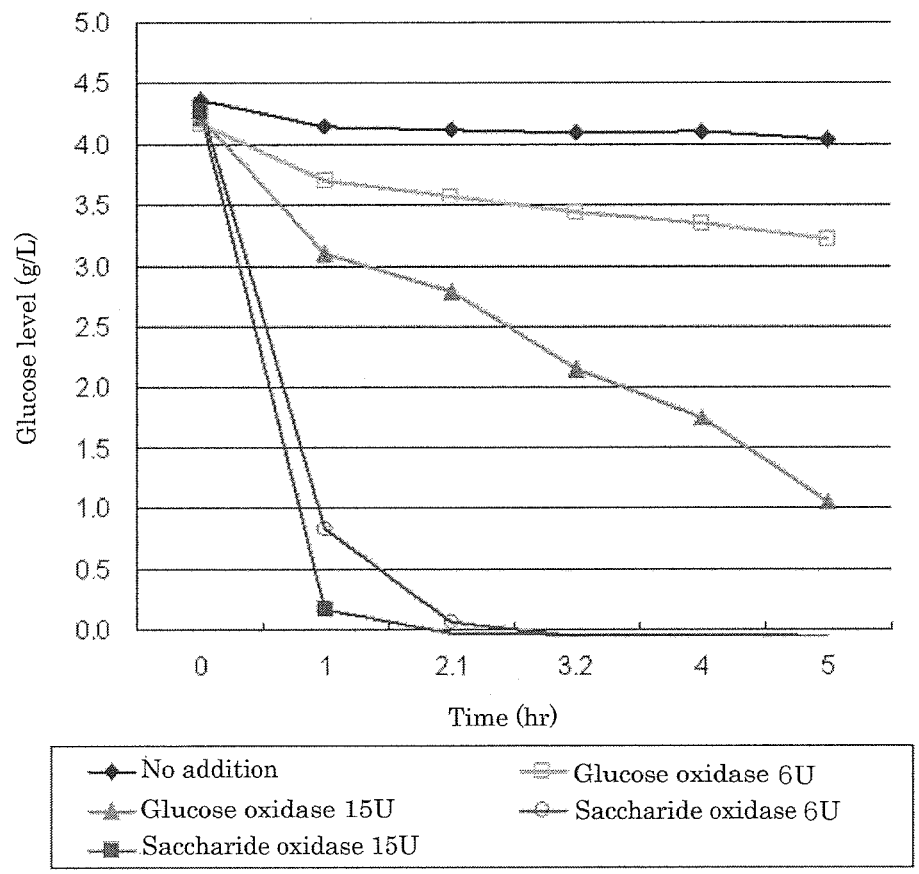
FIG. 6 is a drawing-substituting graph exhibiting the residual glucose level in the desugared egg white in Example 9.

The results are indicated in the drawing-substituting graph of FIG. 6. As indicated in the drawing-substituting graph of FIG. 6, when compared with the case using the glucose oxidase, the case using the protein according to the present invention for desugaring resulted in a significant reduction in the residual glucose level of the desugared egg white.

Example 10: Investigation of Thermal Inactivation Condition after Desugaring of Egg White In Example 10, the thermal inactivation condition after desugaring of egg white was investigated.

Typically, to the egg white prepared as described in Example 9, each 15 U of the protein according to the present invention and the glucose oxidase were added, and the desugaring reaction was conducted for 5 hours. 100 μL of the desugared egg white was subjected to a heat treatment at a temperature of 54, 56, and 58° C. for 1, 3, 5, and 8 minutes, respectively, and then cooled on ice, and the residual activity of each enzyme was measured.

Figure 7:
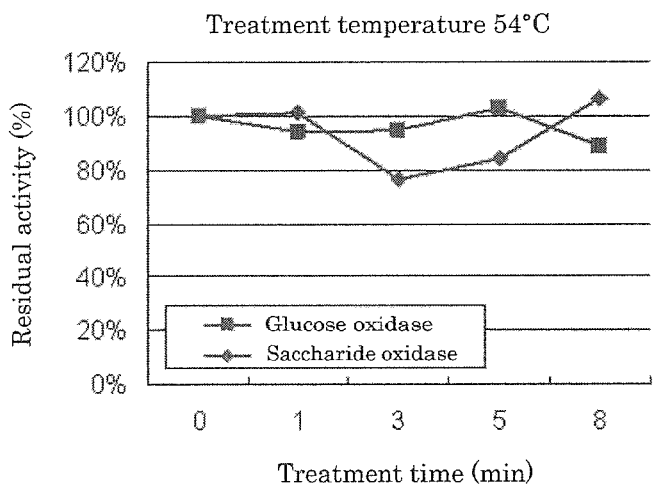
FIG. 7 is a drawing-substituting graph exhibiting the residual activity in the desugared egg white after a heat treatment at 54° C. in Example 10.
Figure 8:
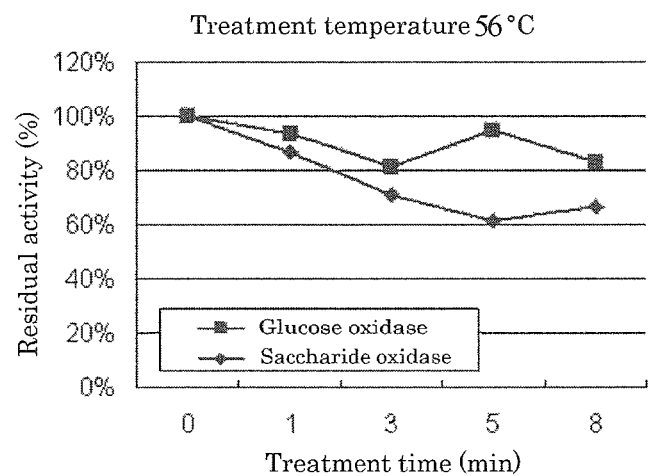
FIG. 8 is a drawing-substituting graph exhibiting the residual activity in the desugared egg white after a heat treatment at 56° C. in Example 10.
Figure 9:
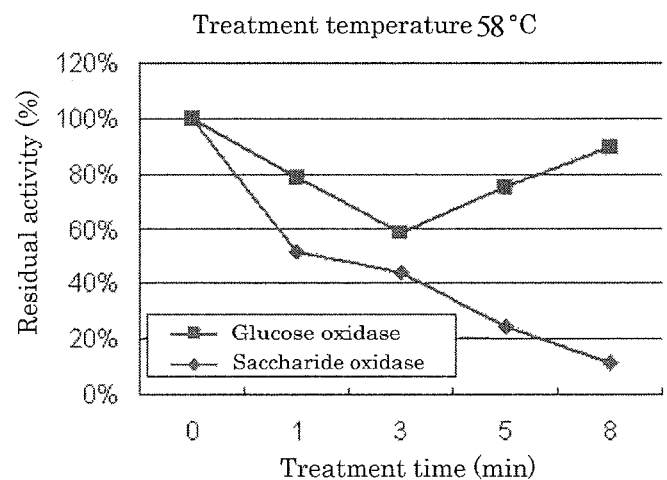
FIG. 9 is a drawing-substituting graph exhibiting the residual activity in the desugared egg white after a heat treatment at 58° C. in Example 10.

The results obtained at 54° C. are shown in FIG. 7, the results obtained at 56° C. are shown in FIG. 8, and the results obtained at 58° C. are shown in FIG. 9. As shown in the drawing-substituting graphs in FIGS. 7 to 9, the heat treatments at 54 and 56° C. caused no substantial reduction in the activity of either the protein according to the present invention or the glucose oxidase, while the heat treatment at 58° C. for 5 minutes or longer caused a significant reduction in the activity of the protein according to the present invention when compared with the glucose oxidase.

Example 11: Production of Bread

In Example 11, the protein purified in the aforementioned Example 1, glucose oxidase ("Hyderase 15" manufactured by Amano Enzyme Inc.), and a hemicellulase ("Hemicellulase "Amano" 90" manufactured by Amano Enzyme Inc.) were used to produce breads.

(1) Method for Preparing Bread

Basic materials for an English bread (hard flour:260 g; sugar:10.9 g; salt:5.2 g; shortening:7.8 g; powdered skim milk:7.8 g; dry yeast:3.1 g; purified water:192 ml), these materials combined with 10 U of the protein purified in the aforementioned Example 1, also these materials combined with 10 U of the protein purified in the aforementioned Example 1 together with 100 ppm of the hemicellulase, and also those combined with 10 U of the glucose oxidase were prepared and subjected to a Home Bakery Model SD-BMS102 (manufactured by Panasonic Corporation).

(2) Measurement of Physical Property

The bread weight and volume (rapeseed substitution method) of each baked sample were measured. Also 2 hours after baking, the volume (rapeseed substitution method) was measured, and each sample bread was placed in a plastic bag, the opening of which was closed using a rubber band, and the bag was stored for 4 days at 25° C. On Day 1 of the storage, the bread was sliced into 2 cm-thick pieces. On Day 1 and Day 4 of the storage, the center of the bread was cut into a cylinder whose diameter was 47 mm. The hardness of each sample bread was measured as a maximum load when compressed by 10 mm at a compression speed of 1 mm/second using SUN RHEO METER COMPAC-100II (manufactured by Sun Scientific Co., Ltd.).

(3) Results

Figure 10:
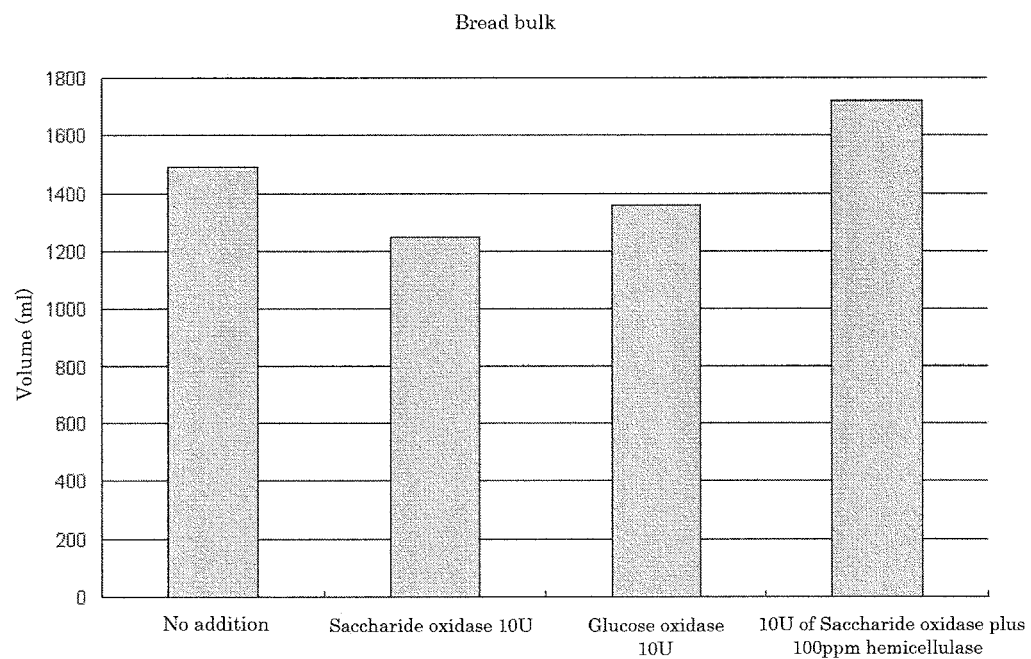
FIG. 10 is a drawing-substituting graph exhibiting the results of the measurement of the volume of the bread in Example 11.
Figure 11:
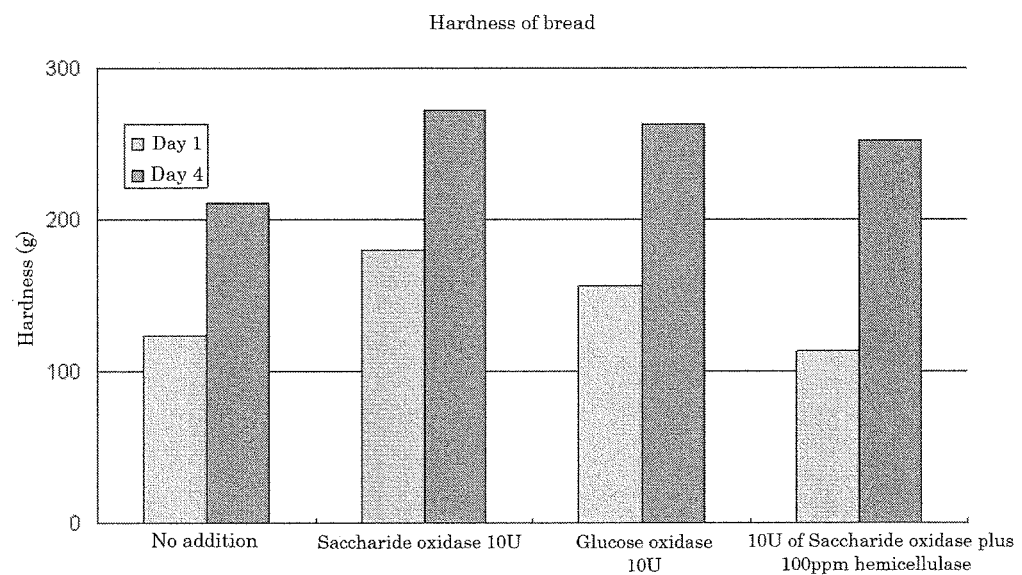
FIG. 11 is a drawing-substituting graph exhibiting the results of the measurement of the hardness of the bread in Example 11.

The volumes measured as described above are shown in FIG. 10, and the bread hardness in FIG. 11. As shown in FIGS. 10 and 11, use of the protein according to the present invention allowed the volume to be reduced, resulting in an increase in the hardness when compared with the glucose oxidase. This means that the effect to tighten the unbaked preparation was higher. Thus, by using the protein according to the present invention, the physical property of the bread can be improved with a smaller amount when compared with a glucose oxidase of the prior art. Also it was possible to achieve a volume similar to that in the absence of the enzyme by use of the hemicellulase in combination. It was also found that, when compared with the glucose oxidase, the protein according to the present invention enabled a reduced stickiness of the unbaked preparation, which less tended to deposit on the machines, resulting in an improved handling upon production.

Example 12: Improvement of Physical Property of Unbaked Bread Preparation (Dough)

In Example 12, the protein purified in the aforementioned Example 1, glucose oxidase ("Hyderase 15" manufactured by Amano Enzyme Inc.), and a hemicellulase ("Hemicellulase "Amano" 90" manufactured by Amano Enzyme Inc.) were used to produce breads.

(1) Method for Preparing Unbaked Bread Preparation

Basic materials for an English bread (hard flour:260 g; sugar:10.9 g; salt:5.2 g; shortening:7.8 g; powdered skim milk:7.8 g; dry yeast:3.1 g; purified water:192 ml), these materials combined with 17 U of the protein purified in the aforementioned Example 1, also these materials combined with 17 U of the glucose oxidase, those combined with 50 ppm of the hemicellulase, and also those combined with 50 ppm of ascorbic acid were prepared and subjected to a Home Bakery Model SD-BMS102 (manufactured by Panasonic Corporation). The machine was started in an unbaked bread preparation course, and after 1 hour the unbaked bread preparation was taken out and placed in a Tosron closed vessel (rectangular shape) and allowed to stand at room temperature for 30 minutes.

(2) Results

The easiness in handling the unbaked preparation prepared as described above was indicated in Table 5 shown below.

TABLE 5

| Easiness in handling unbaked bread preparation | |
|---|---|
| No addition | Δ |
| Saccharide oxidase | ○ |
| Glucose oxidase | Δ |
| Hemicellulase | x |
| Ascorbic acid | ○ |

○: Satisfactory handling
Δ: Somewhat difficult to handle
x: Difficult to handle due to stickiness As shown in Table 5, the unbaked preparations to which the protein according to the present invention or the ascorbic acid were added didn't deposit on the machine, and could be taken out with no difficulty. On the other hand, it was found that the unbaked preparation to which the glucose oxidase was added was somewhat sticky, and the unbaked preparation to which the hemicellulase was added was extremely sticky thereby allowing the dough to remain on hands, resulting in a poor handling during the production. Also it was revealed by visual inspection that the unbaked preparation to which the protein according to the present invention was added had a network appearance.

Example 13: Production of Lactobionic Acid

In Example 13, the protein purified in the aforementioned Example 1 was used to produce lactobionic acid.
(1) Production of Lactobionic Acid
3 ml of a solution containing 0.75 g of lactose monohydrate, 0.225 g of potassium carbonate, and 3 U of the protein purified in the aforementioned Example 1 was added and shaken for 23 hours under the condition involving 40° C. and 160 rpm.
(2) Verification of Lactobionic Acid Production
After the reaction, the sample was boiled for 10 minutes and then centrifuged at 15,000 rpm for 10 minutes. The resultant supernatant was filtered through a 0.45 μm filter and subjected to an HPLC analysis. The HPLC analysis conditions are indicated in Table 6 shown below.

TABLE 6

| Column | TSKgel Amide-80 5 μm |
|---|---|
| Buffer | 40 mM citric acid-sodium citrate (pH 5.0)/acetonitrile = 40/60 |
| Flow rate | 1 mL/min |
| Temperature | 40° C. |
| Injection volume | 10 μm |
| Detection | Differential refractive index detection |

Figure 12:
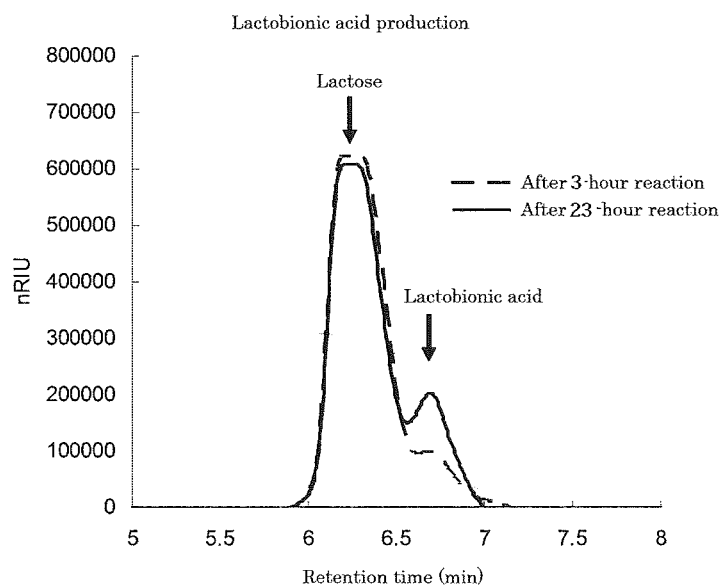
FIG. 12 is a drawing-substituting graph exhibiting the results of the chromatogram of the lactobionic acid production using lactose as a substrate in Example 13.

The results of the aforementioned analysis are shown in FIG. 12. As shown in FIG. 12, the production of the lactobionic acid was verified. Based on these results, it was proven that it is possible to produce the lactobionic acid by an enzymatic method using the protein according to the present invention.

Example 14: Obtaining Gene Fragment Encoding Saccharide Oxidase Derived from *Acremonium chrysogenum* NBRC30055

(a) Isolation of Chromosomal DNA
*Acremonium chrysogenum* NBRC30055 was cultured at 25° C. for 3 days using a round-bottom flask containing 100 mL of YPD medium indicated in Table 7 shown below, and thereafter a Buchner funnel and a Nutsche aspirator were used to filtrate the culture fluid thereby obtaining cells.

TABLE 7

| YPD medium | |
|---|---|
| | (W/V) |
| Yeast extract | 1.00% |
| Peptone | 2.00% |
| Glucose | 2.00% |

After freezing the cells obtained as described above at −80° C. and lyophilized to obtain about 0.3 g of the cells, which was ground together with a spoonful of sea sand using a mortar and pestle and then suspended in 12 ml of Extraction Buffer (1% Hexadecyl trimethyl ammonium bromide, 0.7M sodium chloride, 50 mM Tris-HCl (pH8.0), 10 mM EDTA, 1% mercaptoethanol). After stirring for 30 minutes at room temperature, an equal volume of phenol:chloroform:isoamylalcohol (25:24:1) solution was added, and stirred and centrifuged (1,500 g, 5 minutes, room temperature) to obtain a supernatant. The resultant supernatant was combined with chloroform:isoamylalcohol (24:1) solution, stirred, and then centrifuged (1,500 g, 5 minutes, room temperature) to obtain a supernatant. To the resultant supernatant, an equal volume of isopropanol was added gently. This treatment precipitated the chromosomal DNA, which was centrifuged (20,000 rpm, 10 minutes, 4° C.) to obtain a precipitation, which was washed with 70% ethanol and dried in vacuum. The chromosomal DNA thus obtained was dissolved again in 4 ml of TE, combined with 200 μl of 10 mg/ml RNaseA (manufactured by Sigma Aldrich Co. LLC), and then incubated for 30 minutes at 37° C. Then, 40 μl of 20 mg/ml ProteinaseK, recombinant, PCR Grade (manufactured by Roche Applied Science) solution was added and incubation was conducted for 30 minutes at 37° C., and then an equal volume of phenol:chloroform:isoamylalcohol (25:24:1) solution was added. After stirring and centrifugation (1,500 g, 5 minutes, room temperature), a supernatant was obtained. This washing procedure was repeated twice and the resultant supernatant was combined with chloroform:isoamylalcohol (24:1) solution, stirred, and then centrifuged (1,500 g, 5 minutes, room temperature). The resultant supernatant was combined with 1/10-volume 3M NaOAc (pH4.8) and 2-volume ethanol, and cooled at −80° C. to precipitate the chromosomal DNA. The precipitated chromosomal DNA was recovered by centrifugation (20,000 rpm, 10 minutes, 4° C.). The recovered chromosomal DNA was washed with 70% ethanol, dried in vacuum, and finally dissolved in 400 μl of TE solution to obtain the chromosomal DNA at a concentration of about 1 mg/ml.
(b) Partial Amino Acid Sequencing
The protein purified in the aforementioned Example 1 was analyzed for its amino acid sequence to determine the internal amino acid sequence (SEQ. ID. NOs:1, 2, and 3).
(c) Construction of DNA Probe by PCR
Based on the internal amino acid sequences, two types of the mixed oligonucleotides (SEQ. ID. NOs:4 and 5) were synthesized and used as PCR primers. By using these primers together with the chromosomal DNA of *Acremonium chrysogenum* NBRC30055 as a template, the PCR was conducted under the condition shown below.
<PCR Reaction Solution>
10×PCR Reaction buffer solution (Manufactured by TaKaRa) 5.0 μL dNTP Mixture solution (each 2.5 mM, Manufactured by TaKaRa) 8.0 μL
25 mM MgCl₂ 5.0 μL
50 μM Sense primer 0.5 μL
50 μM Antisense primer 0.5 μL
Distilled water 29.5 μL
Chromosomal DNA solution (100 μg/mL) 1.0 μL
La Taq DNA polymerase (Manufactured by TaKaRa) 0.5 μL
<PCR Condition>
Stage 1: Denaturation (94° C., 1 minute) 1 Cycle
Stage 2: Denaturation (94° C., 30 seconds) 30 Cycles
Annealing (55° C., 30 seconds)
Elongation (72° C., 1.5 minutes)
Stage 3: Elongation (72° C., 3 minutes) 1 Cycle
The resultant about 1-kb DNA fragment was cloned into pGEM-T easy (Manufactured by Promega) and then the base sequence was examined and was found to have a base sequence encoding the aforementioned partial amino acid sequence immediately after the sense primer and immediately before the antisense primer. This DNA fragment was to serve as a DNA probe for the full length gene cloning.

(d) Preparation of Gene Library

As a result of the southern hybridization analysis of the chromosomal DNA of *Acremonium chrysogenum* NBRC30055, an about 3-kb single band which hybridized with the probe DNA was identified in the XbaI cleavage product. For cloning this about 3-kb XbaI DNA fragment, the gene library was prepared as described below.

The chromosomal DNA prepared in the aforementioned (a) was treated with XbaI. 50 µg of the chromosomal DNA, 40 µL of 10×M buffer solution, 40 µL of 10×BSA buffer solution, 302.0 µL of distilled water, and 8.0 µL of XbaI were mixed and the treatment was conducted at 37° C. for 15 hours. The resultant decomposition product was ligated to the XbaI-treated pUC19 vector (Manufactured by TaKaRa) to obtain a gene library.

(e) Screening of Gene Library

The 1-kb DNA fragment obtained in the aforementioned (c) was labeled with DIG-High Prime (manufactured by Roche). This was employed as a DNA probe to screen the gene library obtained in (d) by colony hybridization. From the positive colonies obtained, a plasmid pUCGOOX was obtained.

(f) Determinartion of Base Sequence

The base sequence of the plasmid pUCGOOX obtained as described above was determined according to an ordinary method. The base sequence (1681 bp) encoding saccharide oxidase derived from *Acremonium chrysogenum* NBRC30055 is represented in SEQ. ID. NO:6.

Example 15: Obtaining cDNA Encoding Saccharide Oxidase Derived from *Acremonium chrysogenum* NBRC30055

(a) Isolation of mRNA

Under the culture condition described in the aforementioned Example 1, *Acremonium chrysogenum* NBRC30055 was cultured for 3 days at 25° C. and thereafter a Buchner funnel and a Nutsche aspirator were used to filtrate the culture fluid thereby obtaining cells. Using the cells thus obtained, the total RNA was extracted by RNeasy plant mini-kit (manufactured by QIAGEN). The total RNA thus obtained was subjected to GenElute (Trade Mark) direct mRNA mini-prep kit (manufactured by Sigma Aldrich Co. LLC) to obtain mRNA.

(b) RT-PCR

Based on the base sequence (1681 bp) (SEQ. ID. NO:6) encoding the saccharide oxidase derived from *Acremonium chrysogenum* NBRC30055 obtained in the aforementioned Example 14, two types of oligonucleotides (SEQ. ID. NOs:7 and 8) were synthesized and used as PCR primers. Using the mRNA obtained in the aforementioned (a) as a template together with PrimeScript High Fidelity RT-PCR Kit (Manufactured by TaKaRa), an RT-PCR was conducted under the condition shown below.

<Template RNA Denaturation/Annealing Reaction Solution>
 dNTP Mixture solution (each 10 mM, Manufactured by TaKaRa) 1.0 µL
 2 µM Antisense primer 1.0 µL
 mRNA Solution 4.0 µL
 RNase Free dH$_2$O 4.0 µL
<Template RNA Denaturation/Annealing Condition>
 Stage 1: Denaturation (65° C., 5 minutes) 1 Cycle
 Stage 2: Cooling (4° C., 0.0) 1 Cycle <Template RNA Reverse Transcription Reaction Solution>
 Denatured/annealed reaction solution 10 µL
 5× PrimeScript Buffer (Manufactured by TaKaRa) 4 µL
 RNase Inhibitor (40 U/µl) (Manufactured by TaKaRa) 0.5 µL
 PrimeScript RTase (for 2 steps) (Manufactured by TaKaRa) 0.5 µL
 RNase Free dH$_2$O 5 µL
<Template RNA Reverse Transcription Reaction Condition>
 Stage 1: 42° C., 30 minutes 1 Cycle
 Stage 2: 95° C., 5 minutes 1 Cycle
 Stage 3: 4° C., ∞ 1 Cycle
<PCR Reaction Solution>
 PrimeSTAR Max Premix (2×)(Manufactured by TaKaRa) 50 µL
 20 µM Sense primer 1 µL
 20 µM Antisense primer 1 µL
 Reverse transcription reaction solution 5 µL
 Sterilized water 43 µL
<PCR Condition>
 Stage 1: Denaturation (98° C., 10 seconds) 30 Cycle
 Annealing (55° C., 5 seconds)
 Elongation (72° C., 2 minutes)

(c) Determinartion of Base Sequence

The resultant about 1.5-kb DNA fragment was cloned into an SmaI-treated pBluescript II KS+ vector (manufactured by Stratagene), and thereafter the resultant plasmid pUC-cGOOX was subjected to the base sequencing in accordance with an ordinary method. The cDNA (1518 bp) which encodes saccharide oxidase derived from *Acremonium chrysogenum* NBRC30055 is represented in SEQ. ID. NO:9. The amino acid sequence (amino acid) encoded by SEQ. ID. NO:9 is represented in SEQ. ID. NO:10. In this amino acid sequence, the internal amino acid sequences (SEQ. ID. NOs:1, 2, and 3) determined in the aforementioned Example 15 (b) were found.

Example 16: Expression of Saccharide Oxidase Derived from *Acremonium chrysogenum* NBRC30055 in Mycotic Microorganism (a) Construction of Expression Plasmid Using the two types of oligonucleotides (SEQ. ID. NOs:7 and 8) used in the aforementioned Example 15 together with a template which was a cDNA encoding saccharide oxidase from *Acremonium chrysogenum* NBRC30055 for expression in an *Aspergillus* host cell, a PCR was conducted under the condition shown below.

<PCR Reaction Solution>
 PrimeSTAR Max Premix (2×)(Manufactured by TaKaRa) 25 µL
 20 µM Sense primer 1 µL
 20 µM Antisense primer 1 µL
 Plasmid pUCcGOOX 1 µL
 Sterilized water 22 µL
<PCR Condition>
 Stage 1: Denaturation (98° C., 10 seconds) 33 Cycle
 Annealing (55° C., 5 seconds)
 Elongation (72° C., 15 seconds)

The resultant DNA fragment was identified by an agarose gel electrophoresis, and then purified by NucleoSpinExtractII (manufactured by Nippon Genetics Co., Ltd.).

The expression vector pCSFGP contains a modified promoter described in U.S. Pat. No. 4,495,904 as a regulatory sequence, and flavin adenine dinucleotide-bound glucose dehydrogenase terminator derived from *Aspergillus oryzae* BB-56-derived as well as pyrG gene derived from *Asper-*

*gillus oryzae* BB-56 as a selection marker for fungal transformation. This expression vector also contains an amp gene for selection in *E. coli*.

Figure 13:
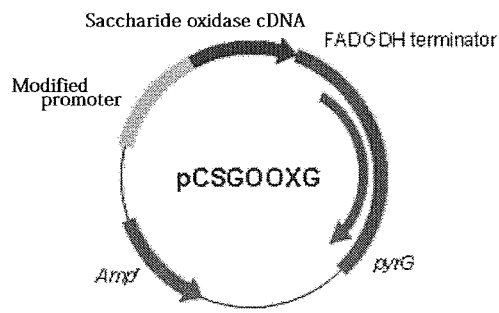
FIG. 13 is a schematic view exhibiting the structure of the expression plasmid pCSGOOXG constructed in Example 16.

The DNA fragment obtained as described above was phosphorylated, and cloned into pCSFGP to form an expression plasmid pCSGOOXG. The plasmid pCSGOOXG thus constructed is shown in FIG. 13.

The expression plasmid was transformed into *E. coli* JM109 Competent Cells (Manufactured by TaKaRa). The transformant containing the correct plasmid was isolated to obtain a plasmid DNA.

(b) Expression of Saccharide Oxidase in Mycotic Microorganism

The transformation of *Aspergillus oryzae* by the expression plasmid pCSGOOXG obtained as described above was conducted as described below. *Aspergillus oryzae* BB-56pyrG- which is a pyrG gene-defect strain was cultured while shaking overnight at 30° C. in the medium described in Table 7 shown above supplemented with 0.2% uridine and 0.1% uracil, and then the cells obtained were suspended in a cell wall lysis solution (20 mg/ml Yatalase (Manufactured by TaKaRa), 0.3 mg/ml Novozym-234 (Novozymes), 0.8M sodium chloride, 10 mM phosphate buffer solution (pH6.0)) and shaken gently for 1 to 2 hours at 30° C. to form protoplasts. The suspension containing the protoplasts was filtered through a nylon filter to remove remaining cells.

*Aspergillus oryzae* BB-56pyrG- was obtained from a parental strain BB-56 by separating a 5-fluoroorotic acid (5-FOA)-resistant strain in accordance with Mol. Gen. Genet. (1987) 210:460-461 followed by selecting an uridine-auxotrophic mutant. *Aspergillus oryzae* BB-56 has been deposited as shown below.

Depositary organization: NITE Biotechnology headquarter, Patent Microorganisms Depositary center (2-5-8, Kazusakamatari, Kisarazu-shi, Chiba, 292-0818 Japan)

Date of deposition (date of reception): May 17, 2006

Deposition number: NITE BP-236

Subsequently, the protoplast obtained by the aforementioned method was used and the method by Turner et al. (Gene, 36, 321-331(1985)) was conducted for preparation of a competent cell and transformation, and several tens of transformants capable of growing in an uridine-free Czapek Dox medium (0.2% NaNO$_3$, 0.1% KH$_2$PO$_4$, 0.05% KCl, 0.05% MgSO$_4$.7H$_2$O, 2% glucose (pH5.5)) were obtained.

The resultant transformants were cultured for 5 days at 30° C. under the culture condition described in the aforementioned Example 1. After the culture, the culture fluid was filtered through a paper filter No. 2 (manufactured by Advantec Toyo Kaisha, Ltd.) to recover the culture filtrate.

(c) Verification of Saccharide Oxidase Expression

Figure 14:
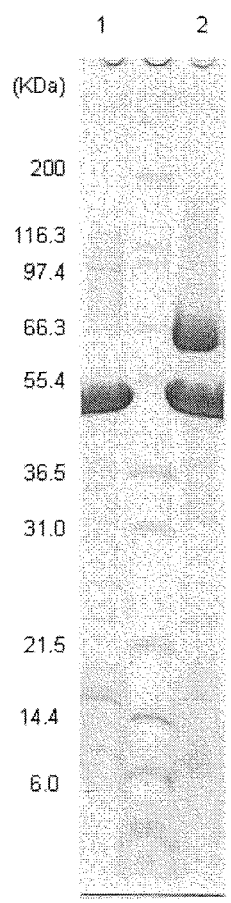
FIG. 14 is a drawing-substituting graph exhibiting the results of an SDS-PAGE of culture filtrate of mycotic microorganism transformant in Example 16. Lane 1: Culture filtrate of *Aspergillus oryzae* BB-56, Lane 2: Culture filtrate of mycotic microorganism transformant.

The samples obtained were subjected to SDS-PAGE. As a result, the pCSGOOXG exhibited significant production of a protein considered to be a saccharide oxidase near about 63 kDa as shown in FIG. 14. Because the culture filtrate of *Aspergillus oryzae* BB-56 as a control exhibited no production of a similar protein, this protein was considered to be attributable to the transduction of the saccharide oxidase cDNA.

The same samples were subjected also to the activity measurement in accordance with the aforementioned saccharide oxidase activity measuring method, and the results are indicated in Table 8 shown below.

TABLE 8

| Saccharide oxidase activity | |
|---|---|
| | (U/ml) |
| pCSGOOXG | 4.2 |
| *Aspergillus oryzae* BB-56 | 0 |

As shown in Table 8, the protein obtained by transduction with the saccharide oxidase cDNA exhibited a significant saccharide oxidase activity when compared with the control, thereby confirming the expression of the intended saccharide oxidase.

SEQUENCE LISTING

SEQ.ID.NO: 1
Ile Ser Glu Val Asp Ala Asp Ser

SEQ.ID.NO: 2
Lys Ser Gly Gly His Ser Tyr

SEQ.ID.NO: 3
Asp Val His Gly Asp

SEQ.ID.NO: 4
aardsyggyg gncacagyta

SEQ.ID.NO: 5
gckccgkkv angtc

SEQ.ID.NO: 6
```
atgagatccc tcgcgccgct cctctccatc
gccgcgctgg cccgggcctc gcctgtcgac acctccctgc
tcacccgcca ggagaccctc aacacctgcc tcgaggccgc
cgagctctcg tacgtcgacg tcaactcgga ggactgggag
gacgccatcg tgccgcacaa cctgcgcgtg cccgtcgtcc
cgcgcgccgt cgtctacgcc accgccacgg agcagatcca
ggccgcggtc aagtgcgccg tcgagagcga gatccgtgtc
tcggccaaga gcggcgggca cagctatgcc tctatgggcc
tgggtggtga ggatggctcc ctcgtcattc agctcgacca
ttggcacgat gtgaccctgc gcgacgacaa caccgccgtg
gtcagcgccg gcacccggct cggtgttgtc gccctcgagc
tgtatgctca gggcaagcgt ggcatctcgc acggaacctg
ccccaggtga gtctttagat gtacatgtat cccatgtatc
caccatgaag catctgccta gaatgtgtga gcgatctgta
ctcatgccgc gcgcgtcaca gtgttggcgt cggtggccac
gtcgtccacg gtggctacgg cttcagctcg cacacccacg
gcctggccct cgacgccgtc gtcggcgcca acgttgtcct
cgccgacggc tcgctcgtgc acgcctccga gacggagaac
acggacctct tctgggccct ccgcggcggc ggctcgtcct
tcggcatcgt cgccgagttc gagttcgaga cgttcgacgt
ctcccacaac ttctcctact tcagcatcga ctccgacatc
tcccaggaga cagccgagga ggccaccgcg tccctgctgg
cgttccagga tgcccttgag gagggactga tggaccgcaa
gctcaacatg cgtctctcgc tcggaaggcc caaggtcact
ctcgaggcgg tctaccatgg cgccaaggag gatggccgca
aggcgctgga gctgtttgat gatatcctgg gcctgaactg
gagctctaac aggacccgag ctaatgaggc tgattggctt
accatgctcg agtcgtggac atacggcgat cccctcaaca
tcacctaccc ctacgaagga gtaagtcgat gagccgggcc
ccatcgcatc attttcccac aggttgactg acaacttatg
ccatatagca tgacaatgcc tacacctcca gcctggtcac
ccgccacatc cccgaagacg ccatggcctc attcatgacc
tactggaagg gggtcggcca agacagggag accccaact
ggtggctgca gatggacgtg cacggcgacg ccaactcgcg
catctccgag gtcgacgccg actccaccgc ctactcgcac
cgcgacaagc tctggctctt ccagttctcc tcgccctga
accccctgcg cccggacccc gaggccgcct ttgccctcgt
caatgggtac atggactcga tcaaggatca cctgggcgac
ggcgagtggg gtcgctatgc caactacatc gactccgagc
tgagcaggga ggacgcgcag acgcagtact ggtccgatca
tctcgacaag ctgcaggcta tcaaggccga gttggatcct
acgcaggtgt tttataaccc acagtccatt
gatccggctg ccgtcgagtg a
```

SEQUENCE LISTING

SEQ.ID.NO: 7
atgagatccc tcgcgccgct c

SEQ.ID.NO: 8
tcactcgacg gcagccggat c

SEQ.ID.NO: 9
atgagatccc tcgcgccgct cctctccatc
gccgcgctgg cccgggcctc gcctgtcgac acctccctgc
tcacccgcca ggagaccctc aacacctgcc tcgaggccgc
cgagctctcg tacgtcgacg tcaactcgga ggactgggag
gacgccatcg tgccgcacaa cctgcgcgtg cccgtcgtcc
cgcgcgccgt cgtctacgcc accgccacgg agcagatcca
ggccgcggtc aagtgcgccg tcgagagcga gatccgtgtc
tcggccaaga gcggcgggca cagctatgcc tctatgggcc
tgggtggtga ggatggctcc ctcgtcattc agctcgacca
ttggcacgat gtgaccctgc gcgacgacaa caccgccgtg
gtcagcgccg gcacccggct cggtgttgtc gccctcgagc
tgtatgctca gggcaagcgt ggcatctcgc acggaacctg
ccccagtgtt cgtcggtg gccacgtcgt ccacgtggtc
tacgcttca gctcgcacac ccacggcctg gccctcgacg
ccgtcgtcgg cgccaacgtt gtcctcgccg acggctcgct
cgtgcacgcc tccgagacgg agaacacgga cctcttctgg
gccctccgcg gcggcggctc gtccttcggc atcgtcgcg
agttcgagtt cgagacgttc gacgtctccc acaacttctc
ctacttcagc atcgactccg acatctccca ggagacagcc
gaggaggcca ccgcgtccct gctggcgttc caggatgccc
ttgaggaggg actgatggac cgcaagctca acatgcgtct
ctcgctcgga aggcccaagg tcactctcga ggcggtctac
catgcgccaa aggaggatgg ccgcaaggcg ctggagctgt
ttgatgatat cctgggcctg aactggagct ctaacaggac
ccgagctaat gaggctgatt ggcttaccat gctcgagtcg
tggacatacg gcgatcccct caacatcacc taccctacg
aaggacatga caatgcctac acctccagcc tggtcacccg
ccacatcccc gaagacgcca tggcctcatt catgacctac
tggaaggggg tcggccaaga cagggagacc ccaactggt
ggctgcagat ggacgtgcac ggcgacgcca actcgcgcat
ctccgaggtc gacgccgact ccaccgccta ctcgcaccgc
gacaagctct ggtcttcca gttctcctcg cccctgaacc
ccctgcgccc ggaccccgag gccgcctttg ccctcgtcaa
tgggtacatg gactcgatca aggatcacct gggcgacggc
gagtggggtc gctatgccaa ctacatcgac tccgagctga
gcagggagga cgcgcagacg cagtactggt ccgatcatct
cgacaagctg caggctatca aggccgagtt ggatcctacg
caggtgtttt ataacccaca gtccattgat ccggctgccg
tcgagtga SEQ.ID.NO: 10
Met Arg Ser Leu Ala Pro Leu Leu Ser
Ile Ala Ala Leu Ala Arg Ala Ser Pro Val Asp Thr
Ser Leu Leu Thr Arg Gln Glu Thr Leu Asn Thr Cys
Leu Glu Ala Ala Glu Leu Ser Tyr Val Asp Val Asn
Ser Glu Asp Glu Asp Ala Ile Val Pro His Asn Leu
Arg Val Pro Val Val Pro Arg Ala Val Val Tyr Ala
Thr Ala Thr Glu Gln Ile Gln Ala Ala Val Lys Cys
Ala Val Glu Ser Glu Ile Arg Val Ser Ala Lys Ser
Gly Gly His Ser Tyr Ala Ser Met Gly Leu Gly Gly
Glu Asp Gly Ser Leu Val Ile Gln Leu Asp His Trp
His Asp Val Thr Leu Arg Asp Asp Asn Thr Ala Val
Val Ser Ala Gly Thr Arg Leu Gly Val Val Ala Leu
Glu Leu Tyr Ala Gln Gly Lys Arg Gly Ile Ser His
Gly Thr Cys Pro Ser Val Gly Val Gly His Val Val
Val His Gly Gly Tyr Gly Phe Ser Ser His Thr His
Gly Leu Ala Leu Asp Ala Val Val Gly Ala Asn Val
Val Leu Ala Asp Gly Ser Leu Val His Ala Ser Glu
Thr Glu Asn Thr Asp Leu Phe Trp Ala Leu Arg Gly
Gly Gly Ser Ser Phe Gly Ile Val Ala Glu Phe Glu
Phe Glu Thr Phe Asp Val Ser His Asn Phe Ser Tyr
Phe Ser Asp Ser Asp Ile Ser Gln Glu Thr Ala Glu
Glu Ala Thr Ala Ser Leu Leu Ala Phe Gln Asp Ala
Leu Glu Glu Gly Leu Met Asp Arg Lys Leu Asn Met
Arg Leu Ser Leu Gly Arg Pro Lys Val Thr Leu Glu
Ala Val Tyr His Gly Ala Lys Glu Asp Gly Arg Lys
Ala Leu Glu Leu Phe Asp Asp Ile Leu Gly Leu Asn
Trp Ser Ser Asn Arg Thr Arg Ala Asn Glu Ala Asp
Trp Leu Thr Met Leu Glu Ser Trp Thr Tyr Gly Asp
Pro Leu Asn Ile Thr Tyr Pro Tyr Glu Gly His Asp
Asn Ala Tyr Thr Ser Ser Leu Val Thr Arg His Ile
Pro Glu Asp Ala Met Ala Ser Phe Met Thr Tyr Trp
Lys Gly Val Gly Gln Asp Arg Glu Thr Pro Asn Trp
Trp Leu Gln Met Asp Val His Gly Asp Ala Asn Ser
Arg Ile Ser Glu Val Asp Ala Asp Ser Thr Ala Tyr
Ser His Arg Asp Lys Leu Trp Leu Phe Gln Phe Ser
Ser Pro Leu Asn Pro Leu Arg Pro Asp Pro Glu Ala
Ala Phe Ala Leu Val Asn Gly Tyr Met Asp Ser Ile
Lys Asp His Leu Gly Asp Gly Glu Trp Gly Arg Tyr
Ala Asn Tyr Ile Asp Ser Glu Leu Ser Arg Glu Asp
Ala Gln Thr Gln Tyr Trp Ser Asp His Leu Asp Lys
Leu Gln Ala Ile Lys Ala Glu Leu Asp Pro Thr Gln
Val Phe Tyr Asn Pro Gln Ser Ile Asp Pro Ala Ala
Val Glu

---

The invention claimed is:

1. A polynucleotide selected from the group consisting of:
   (a) a polynucleotide comprising the nucleotide sequence of SEQ ID NO: 9; and
   (b) a polynucleotide comprising a nucleotide sequence having 90% or more sequence identity with the nucleotide sequence of SEQ ID NO: 9 and encoding a protein having saccharide oxidase activity, and wherein the polynucleotide is a cDNA.

2. A recombinant vector comprising a nucleotide sequence selected from the group consisting of:
   (a) the nucleotide sequence of SEQ ID NO: 9;
   (b) a nucleotide sequence having 90% or more sequence identity with the nucleotide sequence of SEQ ID NO: 9 and encoding a protein having saccharide oxidase activity,
   (c) the nucleotide sequence of SEQ ID NO: 6;
   (d) a nucleotide sequence having 90% or more sequence identity with the nucleotide sequence of SEQ ID NO: 6 and encoding a protein having saccharide oxidase activity,
   (e) a nucleotide sequence encoding the amino acid sequence of SEQ ID NO: 10; and
   (f) a nucleotide sequence encoding an amino acid sequence having 90% or more sequence identity to the amino acid sequence of SEQ ID NO: 10 and encoding a protein having saccharide oxidase activity.

3. A transformant host cell transformed with the recombinant vector of claim 2, wherein the host cell is a microorganism of the genus *Aspergillus*.

4. A method for producing a protein comprising culturing the transformant host cell of claim 3 in a culture medium to produce a protein having saccharide oxidase activity, and collecting the protein having saccharide oxidase activity from the culture.

5. The polynucleotide of claim 1, wherein the polynucleotide consists of the nucleotide sequence of SEQ ID NO: 9.

6. The recombinant vector of claim 2, wherein the nucleotide sequence consists of the nucleotide sequence of SEQ ID NO: 9.

7. A transformant host cell transformed with the recombinant vector of claim 6, wherein the host cell is a microorganism of the genus *Aspergillus*.

8. A method for producing a protein comprising culturing the transformant host cell of claim 7 in a culture medium to produce a protein having saccharide oxidase activity, and collecting the protein having saccharide oxidase activity from the culture.

* * * * *

SEQUENCE LISTING

<160> NUMBER OF SEQ ID NOS: 10

<210> SEQ ID NO 1
<211> LENGTH: 8
<212> TYPE: PRT
<213> ORGANISM: Acremonium chrysogenum

<400> SEQUENCE: 1

Ile Ser Glu Val Asp Ala Asp Ser
1               5

<210> SEQ ID NO 2
<211> LENGTH: 7
<212> TYPE: PRT
<213> ORGANISM: Acremonium chrysogenum

<400> SEQUENCE: 2

Lys Ser Gly Gly His Ser Tyr
1               5

<210> SEQ ID NO 3

```
<211> LENGTH: 5
<212> TYPE: PRT
<213> ORGANISM: Acremonium chrysogenum

<400> SEQUENCE: 3

Asp Val His Gly Asp
1               5

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence : Primer
<220> FEATURE:
<221> NAME/KEY: misc_feature
<222> LOCATION: (12)..(12)
<223> OTHER INFORMATION: n is a, c, g, t or u

<400> SEQUENCE: 4
aardsyggyg gncacagyta                                                  20

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence : Primer
<220> FEATURE:
<221> NAME/KEY: misc_feature
<222> LOCATION: (12)..(12)
<223> OTHER INFORMATION: n is a, c, g, t or u

<400> SEQUENCE: 5
gcckccgkkv angtc                                                       15

<210> SEQ ID NO 6
<211> LENGTH: 1681
<212> TYPE: DNA
<213> ORGANISM: Acremonium chrysogenum

<400> SEQUENCE: 6
atgagatccc tcgcgccgct cctctccatc gccgcgctgg cccgggcctc gcctgtcgac        60
acctccctgc tcacccgcca ggagaccctc aacacctgcc tcgaggccgc cgagctctcg       120
tacgtcgacg tcaactcgga ggactgggag acgccatcg tgccgcacaa cctgcgcgtg        180
cccgtcgtcc cgcgcgccgt cgtctacgcc accgccacgg agcagatcca ggccgcggtc       240
aagtgcgccg tcgagagcga gatccgtgtc tcggccaaga gcggcgggca cagctatgcc       300
tctatgggcc tgggtggtga ggatggctcc ctcgtcattc agctcgacca ttggcacgat       360
gtgaccctgc gcgacgacaa caccgccgtg gtcagcgccg gcaccggct cggtgttgtc       420 gccctcgagc tgtatgctca gggcaagcgt ggcatctcgc acggaacctg ccccaggtga       480
gtctttagat gtacatgtat ccatgtatc caccatgaag catctgccta gaatgtgtga       540
gcgatctgta tcatgccgc gcgcgtcaca gtgttggcgt cggtggccac gtcgtccacg       600
gtggctacgg cttcagctcg cacacccacg gcctggccct cgacgccgtc gtcggcgcca       660
acgttgtcct cgccgacggc tcgctcgtgc acgcctccga cggagaac acggacctct        720 tctgggccct ccgcggcggc ggctcgtcct tcggcatcgt cgccgagttc gagttcgaga       780
cgttcgacgt ctcccacaac ttctcctact cagcatcga ctccgacatc tcccaggaga       840
cagccgagga ggccaccgcg tccctgctgg cgttccagga tgcccttgag gagggactga       900
```

```
tggaccgcaa gctcaacatg cgtctctcgc tcggaaggcc caaggtcact ctcgaggcgg    960
tctaccatgg cgccaaggag gatggccgca aggcgctgga gctgtttgat gatatcctgg   1020
gcctgaactg gagctctaac aggacccgag ctaatgaggc tgattggctt accatgctcg   1080
agtcgtggac atacggcgat cccctcaaca tcacctaccc ctacgaagga gtaagtcgat   1140
gagccgggcc ccatcgcatc attttcccac aggttgactg acaacttatg ccatatagca   1200
tgacaatgcc tacacctcca gcctggtcac ccgccacatc cccgaagacg ccatggcctc   1260
attcatgacc tactggaagg gggtcggcca agacagggag accccaact ggtggctgca    1320
gatggacgtg cacggcgacg ccaactcgcg catctccgag gtcgacgccg actccaccgc   1380
ctactcgcac cgcgacaagc tctggctctt ccagttctcc tcgcccctga accccctgcg   1440
cccggacccc gaggccgcct ttgccctcgt caatgggtac atggactcga tcaaggatca   1500
cctgggcgac ggcgagtggg gtcgctatgc caactacatc gactccgagc tgagcaggga   1560
ggacgcgcag acgcagtact ggtccgatca tctcgacaag ctgcaggcta tcaaggccga   1620
gttggatcct acgcaggtgt tttataaccc acagtccatt gatccggctg ccgtcgagtg   1680
a                                                                  1681

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence : Primer

<400> SEQUENCE: 7
atgagatccc tcgcgccgct c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence : Primer

<400> SEQUENCE: 8
tcactcgacg gcagccggat c                                              21

<210> SEQ ID NO 9
<211> LENGTH: 1518
<212> TYPE: DNA
<213> ORGANISM: Acremonium chrysogenum

<400> SEQUENCE: 9
atgagatccc tcgcgccgct cctctccatc gccgcgctgg cccgggcctc gcctgtcgac     60
acctccctgc tcacccgcca ggagaccctc aacacctgcc tcgaggccgc cgagctctcg    120
tacgtcgacg tcaactcgga ggactgggag gacgccatcg tgccgcacaa cctgcgcgtg    180
cccgtcgtcc cgcgcgccgt cgtctacgcc accgccacga gcagatcca ggccgcggtc     240
aagtgcgccg tcgagagcga gatccgtgtc tcggccaaga gcggcgggca cagctatgcc    300
tctatgggcc tgggtggtga ggatggctcc ctcgtcattc agctcgacca ttggcacgat    360
gtgaccctgc gcgacgacaa caccgccgtg gtcagcgccg gcacccggct cggtgttgtc    420
gccctcgagc tgtatgctca gggcaagcgt ggcatctcgc acggaacctg ccccagtgtt    480
ggcgtcggtg gccacgtcgt ccacggtggc tacggcttca gctcgcacac ccacggcctg    540
gccctcgacg ccgtcgtcgg cgccaacgtt gtcctcgccg acggctcgct cgtgcacgcc    600
```

```
tccgagacgg agaacacgga cctcttctgg gccctccgcg gcggcggctc gtccttcggc    660
atcgtcgccg agttcgagtt cgagacgttc gacgtctccc acaacttctc ctacttcagc    720
atcgactccg acatctccca ggagacagcc gaggaggcca ccgcgtccct gctggcgttc    780
caggatgccc ttgaggaggg actgatggac cgcaagctca acatgcgtct ctcgctcgga    840
aggcccaagg tcactctcga ggcggtctac catggcgcca aggaggatgg ccgcaaggcg    900
ctggagctgt ttgatgatat cctgggcctg aactggagct ctaacaggac ccagagctaat    960 gaggctgatt ggcttaccat gctcgagtcg tggacatacg gcgatcccct caacatcacc   1020 taccccctacg aaggacatga caatgcctac acctccagcc tggtcacccg ccacatcccc   1080
gaagacgcca tggcctcatt catgacctac tggaaggggg tcggccaaga cagggagacc   1140
cccaactggt ggctgcagat ggacgtgcac ggcgacgcca actcgcgcat ctccgaggtc   1200
gacgccgact ccaccgccta ctcgcaccgc gacaagctct ggctcttcca gttctcctcg   1260
cccctgaacc ccctgcgccc ggaccccgag gccgcctttg ccctcgtcaa tgggtacatg   1320
gactcgatca aggatcacct gggcgacggc gagtgggtc gctatgccaa ctacatcgac   1380
tccgagctga gcaggagga cgcgcagacg cagtactggt ccgatcatct cgacaagctg   1440
caggctatca aggccgagtt ggatcctacg caggtgtttt ataacccaca gtccattgat   1500
ccggctgccg tcgagtga                                                  1518

<210> SEQ ID NO 10
<211> LENGTH: 505
<212> TYPE: PRT
<213> ORGANISM: Acremonium chrysogenum

<400> SEQUENCE: 10

Met Arg Ser Leu Ala Pro Leu Leu Ser Ile Ala Ala Leu Ala Arg Ala
1               5                   10                  15

Ser Pro Val Asp Thr Ser Leu Leu Thr Arg Gln Glu Thr Leu Asn Thr
            20                  25                  30

Cys Leu Glu Ala Ala Glu Leu Ser Tyr Val Asp Val Asn Ser Glu Asp
        35                  40                  45

Trp Glu Asp Ala Ile Val Pro His Asn Leu Arg Val Pro Val Val Pro
    50                  55                  60

Arg Ala Val Val Tyr Ala Thr Ala Thr Glu Gln Ile Gln Ala Ala Val
65                  70                  75                  80

Lys Cys Ala Val Glu Ser Glu Ile Arg Val Ser Ala Lys Ser Gly Gly
                85                  90                  95

His Ser Tyr Ala Ser Met Gly Leu Gly Gly Glu Asp Gly Ser Leu Val
            100                 105                 110

Ile Gln Leu Asp His Trp His Asp Val Thr Leu Arg Asp Asp Asn Thr
        115                 120                 125

Ala Val Val Ser Ala Gly Thr Arg Leu Gly Val Ala Leu Glu Leu
    130                 135                 140

Tyr Ala Gln Gly Lys Arg Gly Ile Ser His Gly Thr Cys Pro Ser Val
145                 150                 155                 160

Gly Val Gly Gly His Val His Gly Gly Tyr Gly Phe Ser Ser His
                165                 170                 175

Thr His Gly Leu Ala Leu Asp Ala Val Val Gly Ala Asn Val Val Leu
            180                 185                 190

Ala Asp Gly Ser Leu Val His Ala Ser Glu Thr Glu Asn Thr Asp Leu
        195                 200                 205
```

```
Phe Trp Ala Leu Arg Gly Gly Ser Ser Phe Gly Ile Val Ala Glu
    210             215             220

Phe Glu Phe Glu Thr Phe Asp Val Ser His Asn Phe Ser Tyr Phe Ser
225             230             235             240

Ile Asp Ser Asp Ile Ser Gln Glu Thr Ala Glu Glu Ala Thr Ala Ser
            245             250             255

Leu Leu Ala Phe Gln Asp Ala Leu Glu Glu Gly Leu Met Asp Arg Lys
            260             265             270

Leu Asn Met Arg Leu Ser Leu Gly Arg Pro Lys Val Thr Leu Glu Ala
            275             280             285

Val Tyr His Gly Ala Lys Glu Asp Gly Arg Lys Ala Leu Glu Leu Phe
        290             295             300

Asp Asp Ile Leu Gly Leu Asn Trp Ser Ser Asn Arg Thr Arg Ala Asn
305             310             315             320

Glu Ala Asp Trp Leu Thr Met Leu Glu Ser Trp Thr Tyr Gly Asp Pro
                325             330             335

Leu Asn Ile Thr Tyr Pro Tyr Glu Gly His Asp Asn Ala Tyr Thr Ser
            340             345             350

Ser Leu Val Thr Arg His Ile Pro Glu Asp Ala Met Ala Ser Phe Met
            355             360             365

Thr Tyr Trp Lys Gly Val Gly Gln Asp Arg Glu Thr Pro Asn Trp Trp
    370             375             380

Leu Gln Met Asp Val His Gly Asp Ala Asn Ser Arg Ile Ser Glu Val
385             390             395             400

Asp Ala Asp Ser Thr Ala Tyr Ser His Arg Asp Lys Leu Trp Leu Phe
            405             410             415

Gln Phe Ser Ser Pro Leu Asn Pro Leu Arg Pro Asp Pro Glu Ala Ala
            420             425             430

Phe Ala Leu Val Asn Gly Tyr Met Asp Ser Ile Lys Asp His Leu Gly
            435             440             445

Asp Gly Glu Trp Gly Arg Tyr Ala Asn Tyr Ile Asp Ser Glu Leu Ser
    450             455             460

Arg Glu Asp Ala Gln Thr Gln Tyr Trp Ser Asp His Leu Asp Lys Leu
465             470             475             480

Gln Ala Ile Lys Ala Glu Leu Asp Pro Thr Gln Val Phe Tyr Asn Pro
            485             490             495

Gln Ser Ile Asp Pro Ala Ala Val Glu
            500             505
```